US010960089B2

(12) United States Patent
Arano et al.

(10) Patent No.: US 10,960,089 B2
(45) Date of Patent: Mar. 30, 2021

(54) RADIOLABELED DRUG

(71) Applicant: NATIONAL UNIVERSITY CORPORATION CHIBA UNIVERSITY, Chiba (JP)

(72) Inventors: Yasushi Arano, Chiba (JP); Tomoya Uehara, Chiba (JP)

(73) Assignee: NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 0 days.

(21) Appl. No.: 16/081,141

(22) PCT Filed: Feb. 28, 2017

(86) PCT No.: PCT/JP2017/007875
§ 371 (c)(1),
(2) Date: Aug. 30, 2018

(87) PCT Pub. No.: WO2017/150549
PCT Pub. Date: Sep. 8, 2017

(65) Prior Publication Data
US 2019/0091353 A1    Mar. 28, 2019

(30) Foreign Application Priority Data
Mar. 1, 2016   (JP) .............................. JP2016-038836

(51) Int. Cl.
| | | |
|---|---|---|
| A61K 51/08 | (2006.01) | |
| A61K 51/10 | (2006.01) | |
| C07K 5/08 | (2006.01) | |
| C07K 5/083 | (2006.01) | |
| A61K 47/12 | (2006.01) | |
| A61K 51/04 | (2006.01) | |
| A61P 25/00 | (2006.01) | |

(52) U.S. Cl.
CPC .............. *A61K 51/08* (2013.01); *A61K 47/12* (2013.01); *A61K 51/044* (2013.01); *A61K 51/0474* (2013.01); *A61K 51/1066* (2013.01); *A61K 51/1072* (2013.01); *A61K 51/1093* (2013.01); *C07K 5/08* (2013.01); *C07K 5/081* (2013.01); *A61P 25/00* (2018.01)

(58) Field of Classification Search
None
See application file for complete search history.

(56) References Cited

FOREIGN PATENT DOCUMENTS

WO    WO 2013/081091 A1    6/2013

OTHER PUBLICATIONS

International Search Report and Written Opinion dated Jun. 6, 2017 in connection with PCT/JP2017/007875.

Akizawa et al., Renal uptake and metabolism of radiopharmaceuticals derived from peptides and proteins. Adv Drug Deliv Rev. Sep. 2008;60(12):1319-28. doi: 10.1016/j.addr.2008.04.005. Epub Apr. 23, 2008. Review. PubMed PMID: 18508156.

Uehara et al., (67/68)Ga-labeling agent that liberates (67/68)Ga-NOTA-methionine by lysosomal proteolysis of parental low molecular weight polypeptides to reduce renal radioactivity levels. Bioconjug Chem. Nov. 19, 2014;25(11):2038-45. doi: 10.1021/bc5004058. Epub Oct. 22, 2014.

Uehara et al., Hoshasei Gallium Hyoshiki Kotai Fragment no Hi Tokuiteki Jin Shuseki o Teigen saseru Hyoshiki Yakuzai no Kaihatsu. Abstracts of Annual Meeting of Pharmaceutical Society of Japan. Mar. 4, 2016:27L-am01.

Uehara et al., Radio-gallium labeling reagent for antibody fragments with low renal radioactivity levels. Annual Scientific Meeting of the Japanese Society of Nuclear Medicine Yoshishu. Oct. 20, 2016:s266[M1IXD2].

(Continued)

*Primary Examiner* — Jennifer Lamberski
(74) *Attorney, Agent, or Firm* — Buchanan Ingersoll & Rooney PC

(57) ABSTRACT

Described are: [1] a compound represented by the formula (1), [2] a compound containing the compound according to [1] and a target molecule recognition element bonded thereto, [3] a metal complex compound containing one kind of a metal selected from a radioactive metal and a radioactive atom-labeled metal, and the compound according to [1] or [2], which is coordinated to the metal, [4] a drug for preparing a radiolabeled drug, containing the compound according to [1] or [2], [5] use of the compound according to [1] or [2], for producing a radiolabeled drug, [6] a radiolabeled drug containing the metal complex compound according to [3], and [7] a radiodiagnostic imaging agent containing the metal complex compound according to [3]:

8 Claims, 6 Drawing Sheets

(56) References Cited

OTHER PUBLICATIONS

The extended European search report dated Oct. 1, 2019, by the European Patent Office in corresponding European Patent Application No. 17760014.85. (7 pages).
Li et al., "Reduction of Kidney Uptake in Radiometal Labeled Peptide Linkers Conjugated to Recombinant Antibody Fragments. Site-Specific Conjugation of DOTA-Peptides to a Cys-Diabody," Bioconjugate Chemical, (2002) vol. 13, pp. 985-995.
Communication pursuant to Article 94(3) EPC dated Aug. 5, 2020, by the European Patent Office in corresponding European Patent Application No. 17760014.5. (4 pages).
Notice of Reasons for Refusal dated Feb. 10, 2021, by the Japanese Patent Office in corresponding Japanese Patent Application No. 2018-503339 and an English translation of the Notice. (8 pages).

[Fig. 1]
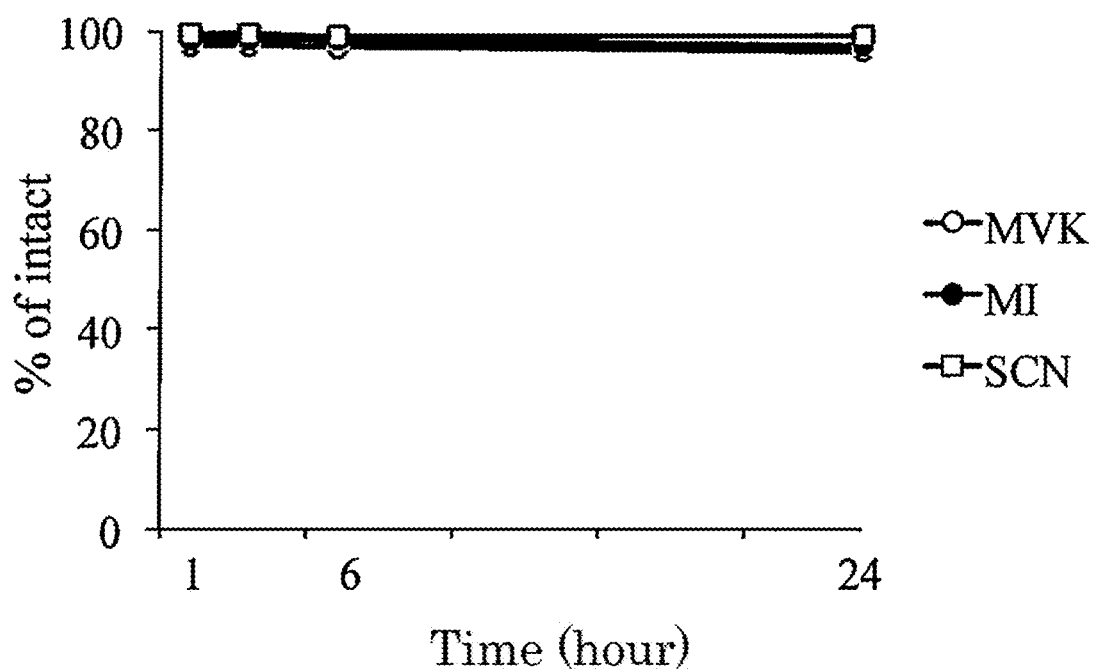

[Fig. 2]
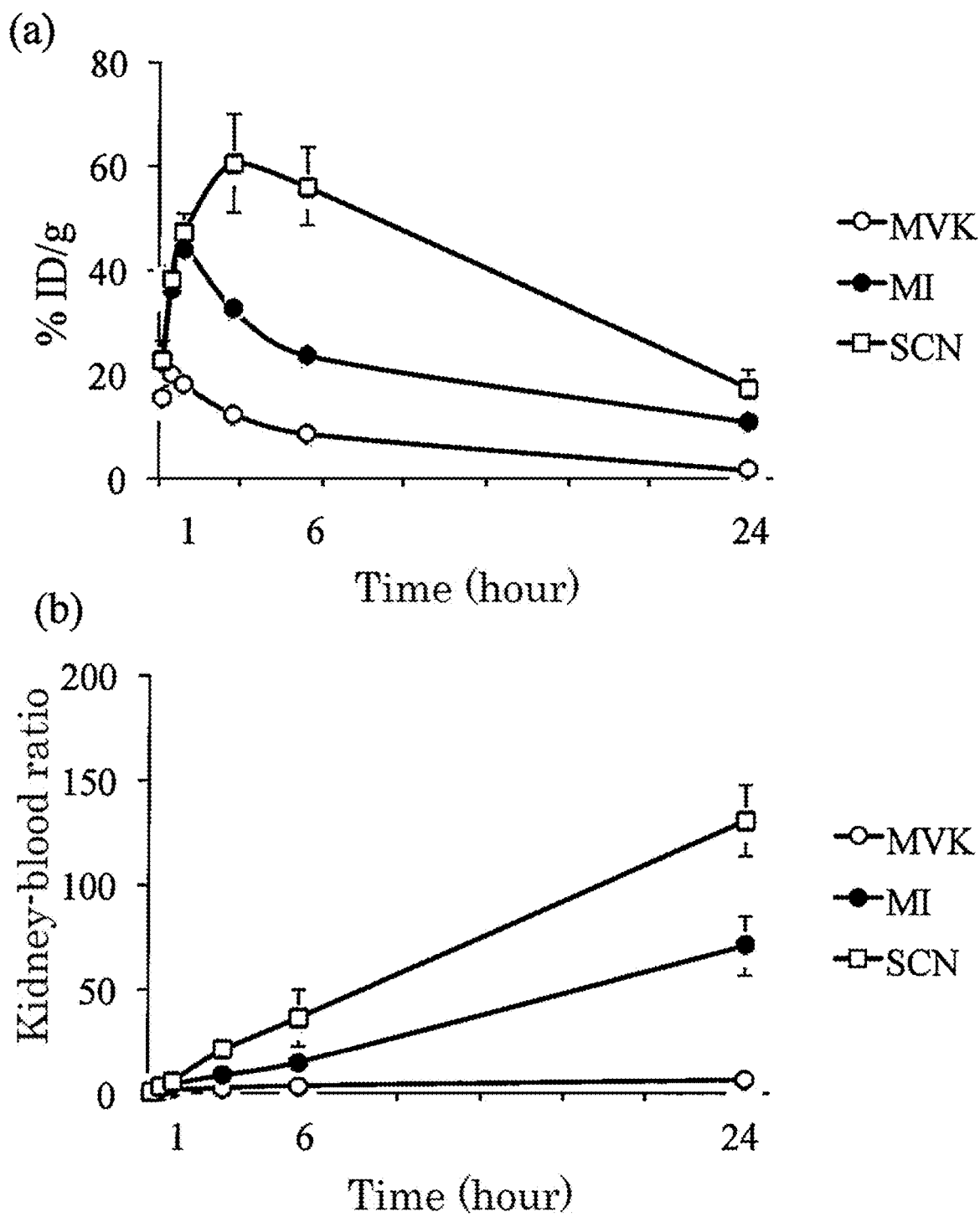

[Fig. 3]
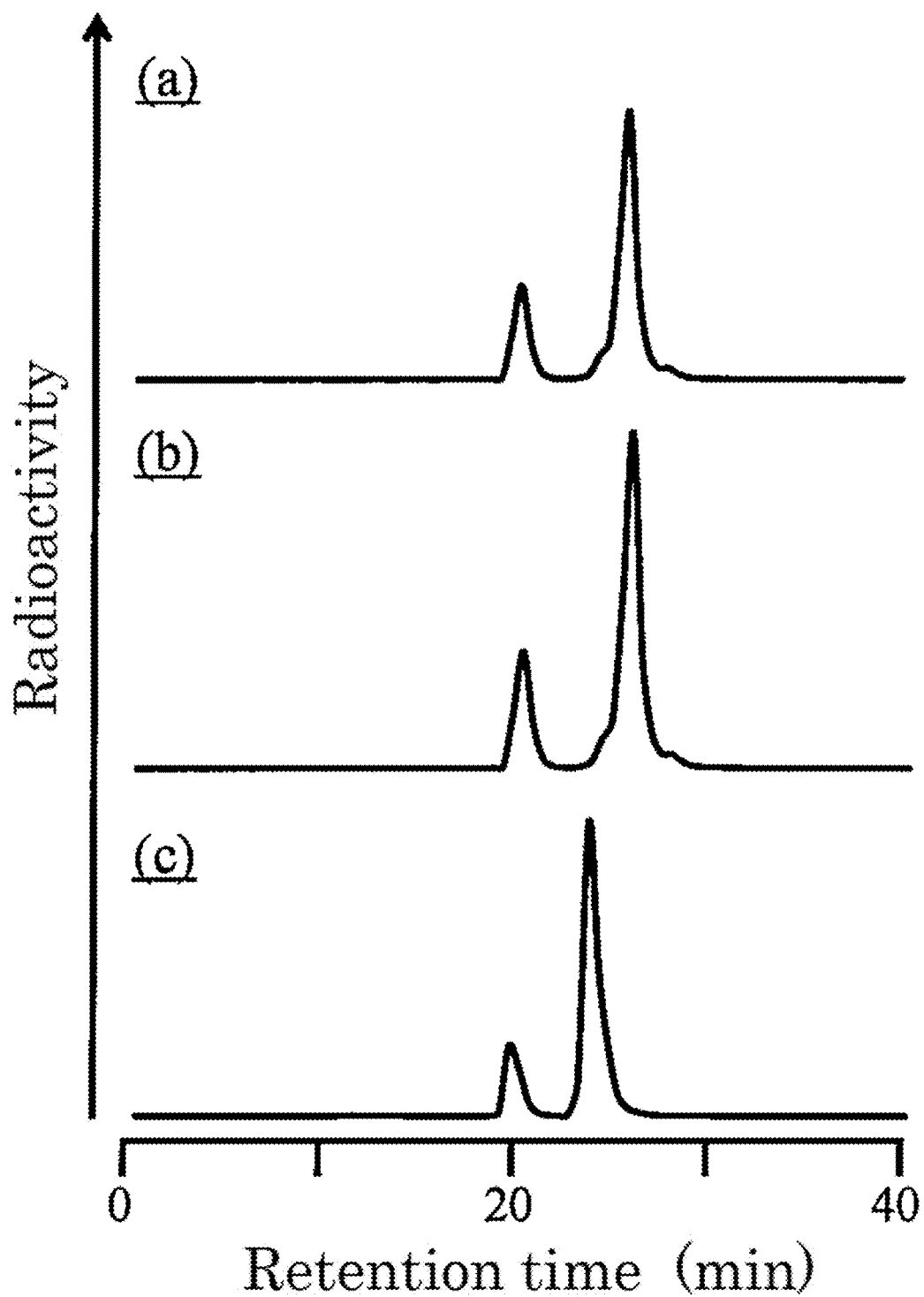

[Fig. 4]
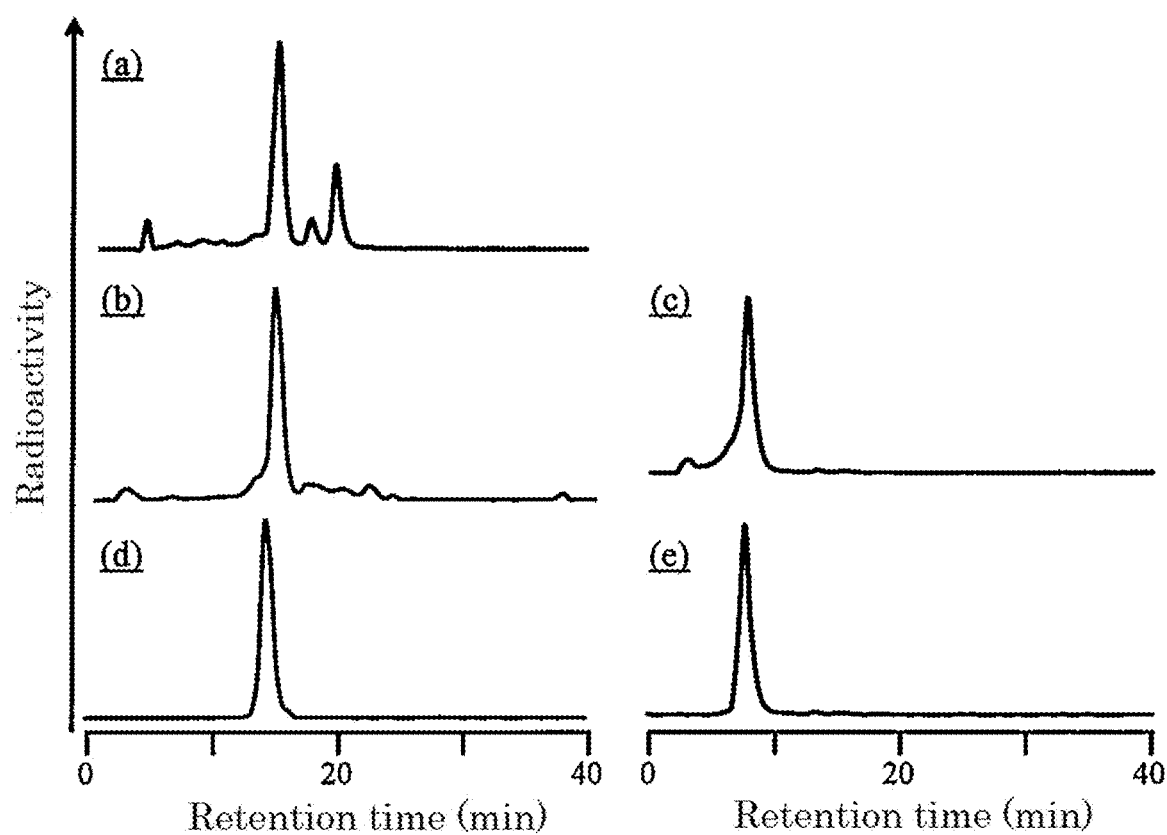

[Fig. 5]
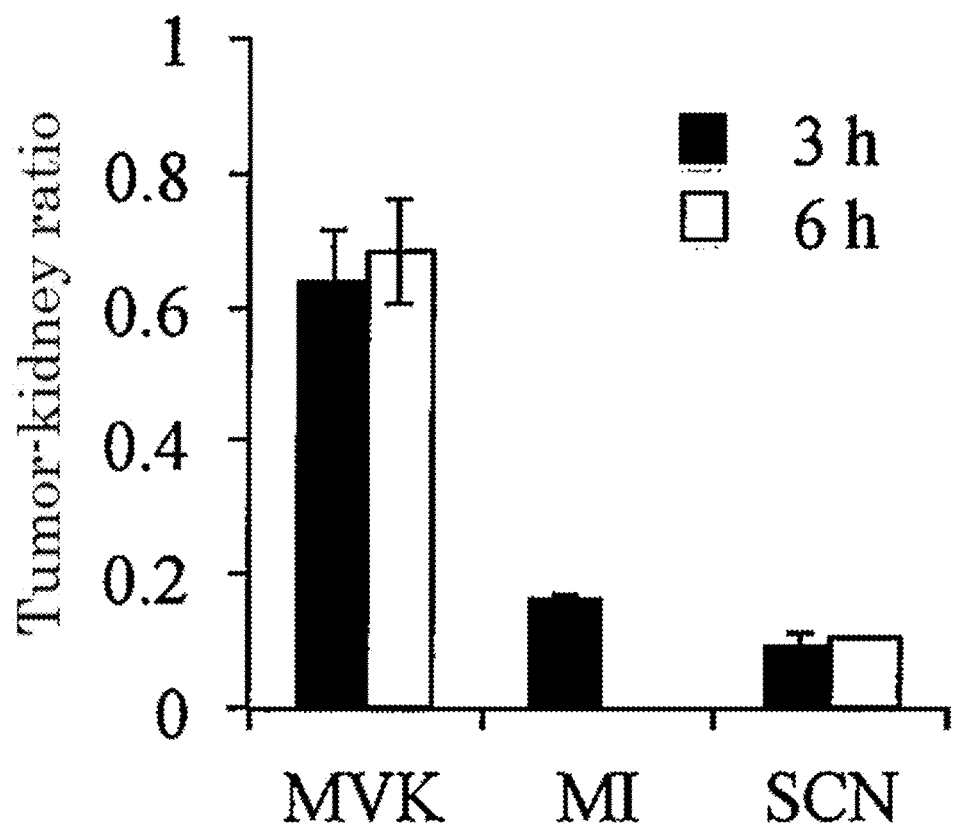
[Fig. 6]
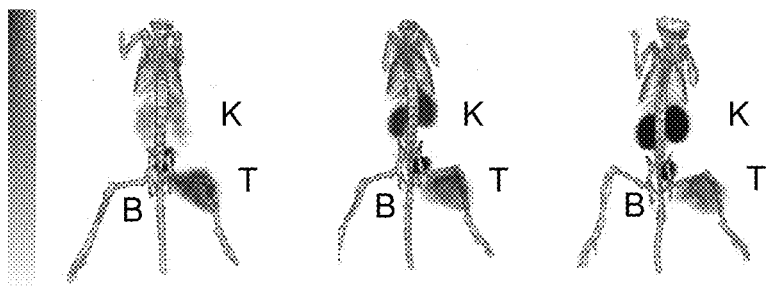

[Fig. 7]
$^{64}$Cu-MVK-Fab    $^{64}$Cu-SCN-Fab

RADIOLABELED DRUG

This Application is a National Stage filing under 35 U.S.C. 371 of International Patent Application No. PCT/JP2017/007875, filed Feb. 28, 2017, which claims priority benefits under 35 U.S.C. § 119(a)-(d) or 35 U.S.C. § 365(b) of Japanese Application Number 2016-038836, filed Mar. 1, 2016. The entire contents of these applications are incorporated herein by reference in their entirety.

TECHNICAL FIELD

The present invention relates to a novel compound, a radiolabeled drug containing the same, a drug for preparing the radiolabeled drug, and the like.

BACKGROUND ART

A radiological imaging diagnosis, such as single photon emission computed tomography (which may be hereinafter referred simply to as "SPECT") and positron emission tomography (which may be hereinafter referred simply to as "PET"), has been performed by using a radiolabeled drug. Various radionuclides have been used for the radiological imaging diagnosis, and among these, radioactive gallium can be applied to both the instruments including SPECT, to which gallium-67 ($^{67}$Ga) can be applied, and PET, to which gallium-68 ($^{68}$Ga) can be applied. In particular, $^{68}$Ga is receiving attention in recent years since $^{68}$Ga can be eluted from a generator using germanium-68. Due to the short half-life period of $^{68}$Ga of 68 minutes, a peptide having a small molecular weight, such as a low molecular weight antibody having a rapid blood clearance, is used as a label matrix. However, in the case where a radioisotope-labeled (RI-labeled) low molecular weight peptide is administered to a living body, a non-specific accumulation in a kidney is observed in addition to the specific accumulation in the target tissue. In this case, imaging of the target tissue that is near the kidney may be difficult. The accumulation of radioactivity in a kidney (which may be hereinafter referred to as "renal accumulation") occurs in such a mechanism that the RI-labeled low molecular weight peptide incorporated into the kidney is transported to lysosomes, and metabolized to form a radioactive metabolite, which remains in the kidney.

For solving the problem, the radioactive gallium-labeled drug described in NPL 1 reduces the renal accumulation significantly as compared to the ordinary methods in such a mechanism that through utilization of the excretion of $^{67}$Ga-NOTA-Bn-Met (see the formula in the description of the literature) from the renal lysosome fraction to urine, $^{67}$Ga-NOTA-Bn-Met is liberated in the lysosomes after incorporating the radioactive gallium-labeled antibody fragment into the renal tissue.

CITATION LIST

Non-Patent Literature

NPL 1: Bioconjugate Chem., 2014, 25, 2038-2045

SUMMARY OF INVENTION

Technical Problem

The half-life period of $^{68}$Ga is as short as 68 minutes, and therefore it is preferred to reduce the renal accumulation thereof in the early stage after the administration thereof. In the method described above, the renal radioactivity is significantly reduced after one hour after the administration as compared to the ordinary labeling methods, but cannot be reduced in the early stage before one hour after the administration.

The present invention relates to a compound, etc. capable of providing a radiolabeled drug that can reduce the renal accumulation thereof in the early stage after the administration thereof.

Solution to Problem

The present invention relates to the following inventions.

[1] A compound represented by the following formula (1) or a pharmacologically allowable salt thereof:

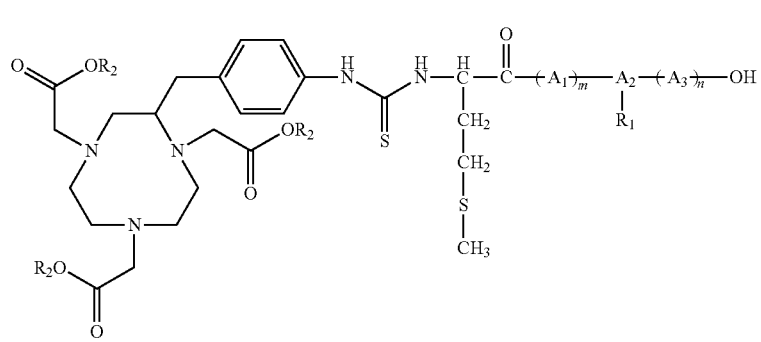

wherein
$A_1$ represents an amino acid residue,
m represents an integer of from 0 to 3,
$A_2$ represents a residue of an amino acid having an amino group or a carboxy group on a side chain thereof,
$A_3$ represents an amino acid residue,
n represents an integer of from 0 to 3,
$R_1$ represents a group that is bonded to the amino group or the carboxy group on the side chain of $A_2$, and has a functional group capable of being bound to a polypeptide or a linking group thereof, and
$R_2$ each independently represent a hydrogen atom or a hydrocarbon group having from 1 to 8 carbon atoms,
provided that $R_1$ may form a heterocyclic group having from 3 to 10 carbon atoms including a nitrogen atom of the amino group on the side chain of $A_2$ as one of the ring-forming atoms.

[2] A compound or a pharmacologically allowable salt thereof, containing the compound or a pharmacologically allowable salt thereof according to the item [1] and a target molecule recognition element bonded thereto.

[3] A metal complex compound or a pharmacologically allowable salt thereof, containing one kind of a metal selected from a radioactive metal and a radioactive atom-labeled metal, and the compound or a pharmacologically allowable salt thereof according to the item [1] or [2], which is coordinated to the metal.

[4] A drug for preparing a radiolabeled drug, containing the compound or a pharmacologically allowable salt thereof according to the item [1] or [2].

[5] Use of the compound or a pharmacologically allowable salt thereof according to the item [1] or [2], for producing a radiolabeled drug.

[6] A radiolabeled drug containing the metal complex compound or a pharmacologically allowable salt thereof according to the item [3].

[7] A radiodiagnostic imaging agent containing the metal complex compound or a pharmacologically allowable salt thereof according to the item [3].

[8] The compound or a pharmacologically allowable salt thereof according to the item [1] or [2], wherein the compound or a pharmacologically allowable salt thereof is for preparing a radiolabeled drug.

[9] Use of the metal complex compound or a pharmacologically allowable salt thereof according to the item [3], for producing a radiolabeled drug.

[10] Use of the metal complex compound or a pharmacologically allowable salt thereof according to the item [3], for a radiological imaging diagnosis.

[11] A radiological imaging diagnostic method including administrating the metal complex compound or a pharmacologically allowable salt thereof according to the item [3].

[12] A kit containing, as discrete package units, the compound or a pharmacologically allowable salt thereof according to the item [1], or a compound or a pharmacologically allowable salt thereof containing the compound or a pharmacologically allowable salt thereof according to the item [1] and a target molecule recognition element bonded thereto, and a drug containing one kind of a metal selected from a radioactive metal and a radioactive atom-labeled metal.

Advantageous Effects of Invention

According to the present invention, a compound, etc. capable of providing a radiolabeled drug that can reduce the renal accumulation thereof in the early stage after the administration thereof can be provided.

BRIEF DESCRIPTION OF DRAWINGS

FIG. 1 shows the results of studies on the stability of the radioactive metal-labeled Fab in mouse plasma.

FIG. 2 shows the time-dependent changes of (a) the renal radioactivity (i.e., the time-radiation dose curve in the kidney) and (b) the radioactivity with respect to the kidney-blood ratio.

FIG. 3 shows the analysis results of the radioactivity in urine by SE-HPLC until after 6 hours from the administration of (a)$^{67}$Ga-NOTA-MVK-Fab, (b) $^{67}$Ga-NOTA-MI-Fab, and (c)$^{67}$Ga-NOTA-SCN-Fab.

FIG. 4 shows the analysis results of the radioactivity in urine by RP-HPLC until after 6 hours from the administration of (a)$^{67}$Ga-NOTA-MVK-Fab, (b) $^{67}$Ga-NOTA-MI-Fab, and (c)$^{67}$Ga-NOTA-SCN-Fab, and the analysis results by RP-HPLC of (d) the authentic sample of $^{67}$Ga-NOTA-Met and (e) the authentic sample of $^{67}$Ga-NOTA-Lys.

FIG. 5 shows the tumor-kidney ratio of $^{67}$Ga-NOTA-MVK-Fab, $^{67}$Ga-NOTA-MI-Fab, and $^{67}$Ga-NOTA-SCN-Fab.

FIG. 6 shows the SPECT/CT images after 3 hours from the administration of the $^{67}$Ga-labeled Fab solutions to the SY subcutaneous tumor model mice.

FIG. 7 shows the PET images after 3 hours from the administration of $^{64}$Cu-NOTA-MVK-Fab (which is shown as $^{64}$Cu-MVK-Fab in the figure) and $^{64}$Cu-NOTA-Fab (which is shown as $^{64}$Cu-SCN-Fab in the figure) to the normal mice.

DESCRIPTION OF EMBODIMENT

[Compound, etc.]
<Compound (1), etc.>

The compound or a pharmacologically allowable salt thereof of the present invention (which may be hereinafter referred simply to as a "compound (1), etc.") is represented by the following formula (1):

$$\text{(1)}$$

wherein
$A_1$ represents an amino acid residue,
m represents an integer of from 0 to 3,
$A_2$ represents a residue of an amino acid having an amino group or a carboxy group on a side chain thereof,
$A_3$ represents an amino acid residue,
n represents an integer of from 0 to 3,
$R_1$ represents a group that is bonded to the amino group or the carboxy group on the side chain of $A_2$, and has a functional group capable of being bound to a target molecule recognition element or a linking group thereof, or a hydrogen atom of the amino group or the carboxy group on the side chain of $A_2$, and
$R_2$ each independently represent a hydrogen atom or a hydrocarbon group having from 1 to 8 carbon atoms,
provided that $R_1$ may form a heterocyclic group having from 3 to 10 carbon atoms including a nitrogen atom of the amino group on the side chain of $A_2$ as one of the ring-forming atoms.

According to the present invention, a compound capable of providing a radiolabeled drug that can reduce the renal accumulation thereof in the early stage after the administration thereof can be provided. With the radiolabeled drug of the present invention having the feature of low renal accumulation, abdominal lesions can be easily detected and diagnosed in a radiological imaging diagnosis owing to the low abdominal background radioactivity. Furthermore, the radiolabeled drug of the present invention can be specifically bound to a target site owing to the target molecule recognition element thereof, and thus can be efficiently accumulated in the target site. The radiolabeled drug of the present invention can enhance the sensitivity and the accuracy of a radiological imaging diagnosis owing to these characteristics.

The mechanism of the effects obtained by the present invention is not clear, but can be considered as follows. In the following description, cases using $^{67}$Ga as the metal will be described as examples.

It is considered that the renal accumulation of radioactivity can be reduced in the case where in the incorporation of the administered radiolabeled drug into the renal cells, a urinary excretable radioactive metabolite can be efficiently liberated therefrom. As for the radioactive metabolite, $^{67}$Ga-NOTA-Bn-Met shown below can be assumed.

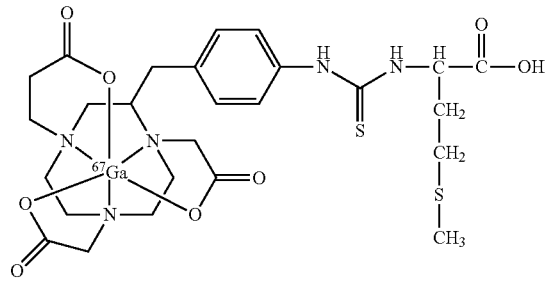

$^{67}$Ga-NOTA-Bn-Met

In the method of NPL 1, the renal radioactivity can be significantly reduced after one hour after the administration thereof as compared to the ordinary labeling methods, but cannot be reduced in the early stage after the administration. It is considered that this is because the radioactive gallium-labeled drug incorporated into the renal cells is transported to lysosomes, and then $^{67}$Ga-NOTA-Bn-Met is liberated therefrom.

A substrate sequence of renal brush border membrane enzyme is inserted between the polypeptide and $^{67}$Ga-NOTA-Bn-Met for facilitating the efficient liberation of $^{67}$Ga-NOTA-Bn-Met in the incorporation of the administered radiolabeled drug into the renal cells, and thus it is considered that $^{67}$Ga-NOTA-Bn-Met is liberated from the polypeptide before the incorporation into the renal cells, so as to reduce the incorporation of the radioactive substance into the kidney, and thereby the renal accumulation thereof can be reduced from the early stage.

In particular, it is considered that the carboxy end of the amino acid sequence is not chemically modified, thereby facilitating the liberation of $^{67}$Ga-NOTA-Bn-Met by the renal brush border membrane enzyme, and thus the effects of the present invention can be obtained.

As for the compound (1), etc. of the present invention, in the formula (1), $A_1$ preferably represents a lipid-soluble amino acid residue, and more preferably a residue of valine, leucine, isoleucine, or phenylalanine, from the standpoint of the reduction of the renal accumulation in the early stage from the administration, and is further preferably a residue of valine from the standpoint of the achievement of the conspicuous effect of reducing the renal accumulation in the early stage from the administration.

m represents an integer of from 0 to 3, and preferably 1.

$A_2$ represents a residue of an amino acid having an amino group or a carboxy group on a side chain thereof, preferably a residue of lysine, ornithine, arginine, aspartic acid, or glutamic acid, more preferably a residue of lysine, ornithine, or arginine, and further preferably a residue of lysine, from the standpoint of the introduction of the functional group capable of being bound to a polypeptide or a linking group thereof.

The compound, etc. may have an additional amino acid residue as $A_3$. An arbitrary amino acid may be used as $A_3$.

n represents an integer of from 0 to 3, and preferably 0.

$R_1$ represents a group that has a functional group capable of being bound to a target molecule recognition element or a linking group thereof, or a hydrogen atom of the amino group or the carboxy group on the side chain of $A_2$, and is bonded to the amino group or the carboxy group on the side chain of $A_2$. $R_1$ may form a heterocyclic group having from 3 to 10 carbon atoms including a nitrogen atom of the amino group on the side chain of $A_2$ as one of the ring-forming atoms.

$R_1$ functions as a spacer, and can bond a target molecule recognition element, such as a polypeptide, to the compound of the present invention via the functional group. $R_1$ is bonded to the amino group or the carboxy group on the side chain of $A_2$, and thereby can bond the compound of the present invention to the polypeptide without chemical modification of the terminal of the amino acid sequence.

$R_1$ may be bonded to the nitrogen atom of the amino group on the side chain, or may form an ester bond with the carboxy group on the side chain.

The functional group capable of being bound to a target molecule recognition element or a linking group thereof of $R_1$ is not particularly limited, and examples thereof include at least one kind of a functional group (which may be hereinafter referred to as a "functional group a") selected from the group consisting of a carboxy group or an active ester thereof; a group having a C=C bond, e.g., a maleimide group and an acryloyl group; a carbamoyl group, an isothiocyanate group, and an amino group. Examples of the active ester of a carboxy group include a chloroacetyl group, a bromoacetyl group, and an iodoacetyl group. Among these, the functional group a is preferably a group having a C=C bond, or a carbamoyl group.

The total number of carbon atoms of $R_1$ is not particularly limited, and is preferably 1 or more, more preferably 2 or more, and further preferably 3 or more, and is preferably 20 or less, more preferably 10 or less, and further preferably 8 or less.

Examples of $R_1$ include an acyl group having from 2 to 20 carbon atoms having the functional group a, an alkyl group having from 2 to 20 carbon atoms having the functional group a, an alkylcarbamoyl group having from 2 to 20 carbon atoms having the functional group a, and an alkylthiocarbamoyl group having from 2 to 20 carbon atoms having the functional group a.

In the case where $R_1$ forms a heterocyclic group, the heterocyclic group is preferably a maleimide group.

In the case where $R_1$ forms a heterocyclic group, the number of carbon atoms of the heterocyclic group is preferably from 3 to 10, more preferably from 3 to 5, and further preferably 4 or 5.

$R_1$ may be a hydrogen atom of the amino group or the carboxy group on the side chain of $A_2$. In other words, the amino group or the carboxy group on the side chain of $A_2$ may not be modified.

$R_1$ is preferably a heterocyclic group having from 3 to 10 carbon atoms including a nitrogen atom of the amino group on the side chain of $A_2$ as one of the ring-forming atoms, and more preferably a maleimide group including a nitrogen atom of the amino group on the side chain of $A_2$ as one of the ring-forming atoms.

$R_2$ each independently represent a hydrogen atom or a hydrocarbon group having from 1 to 8 carbon atoms.

The hydrocarbon group of $R_2$ is not particularly limited, and is preferably a hydrocarbon group that is used as a protective group, and examples thereof include a methyl group, an ethyl group, a t-butyl group, and a benzyl group.

$R_2$ is preferably a hydrogen atom among these.

The compound (1) of the present invention described above is preferably a compound represented by the following formula (1a):

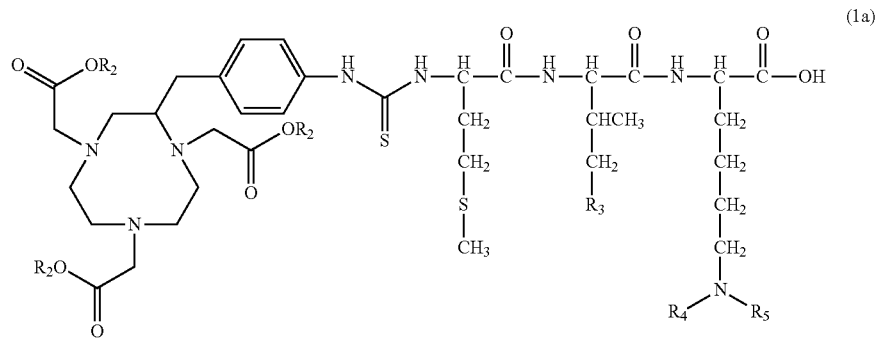

(1a)

wherein $R_2$ each independently represent a hydrogen atom or a hydrocarbon group having from 1 to 8 carbon atoms; $R_3$ represents a hydrogen atom or a methyl group; and $R_4$ and $R_5$ each independently represent a hydrogen atom, an acyl group having from 2 to 20 carbon atoms having a functional group a, an alkyl group having from 2 to 20 carbon atoms having a functional group a, an alkylcarbamoyl group having from 2 to 20 carbon atoms having a functional group a, or an alkylthiocarbamoyl group having from 2 to 20 carbon atoms having a functional group a, provided that $R_4$ and $R_5$ may form a heterocyclic ring including the adjacent nitrogen atom, and in this case, the group represented by the following formula:

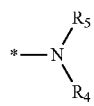

is a group represented by the following formula:

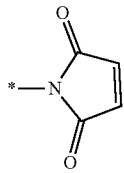

$R_4$ and $R_5$ each are preferably an acyl group having from 2 to 20 carbon atoms having a functional group a, and more preferably an acyl group having from 3 to 6 carbon atoms having a carbamoyl group. Examples of the acyl group having from 3 to 6 carbon atoms having a carbamoyl group include a group represented by the formula: —C(=O)$(CH_2)_a$(=O)$NH_2$ (wherein a represents an integer of from 1 to 4).

Preferred examples of the compound (1) of the present invention include the following compounds 1-1 to 1-4.

1-1: NOTA-MVK(mal)

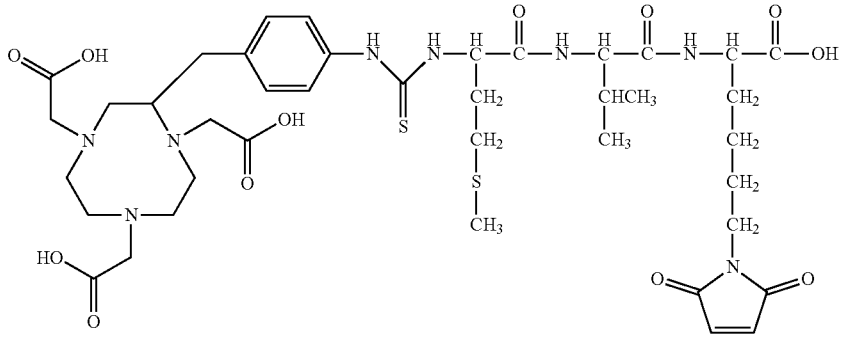

1-2: NOTA-MVK

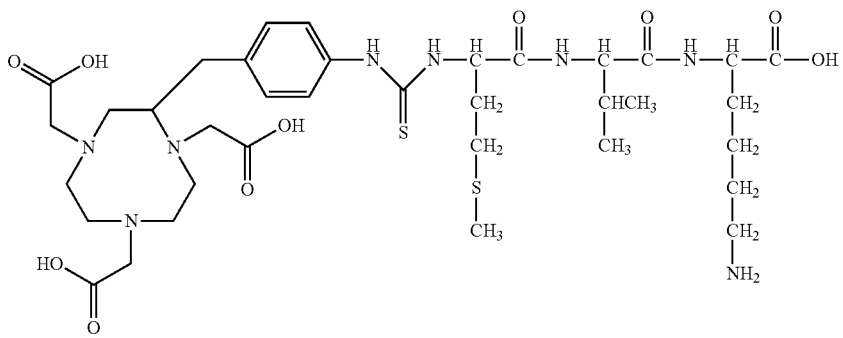

1-3: NOTA-MIK(mal)

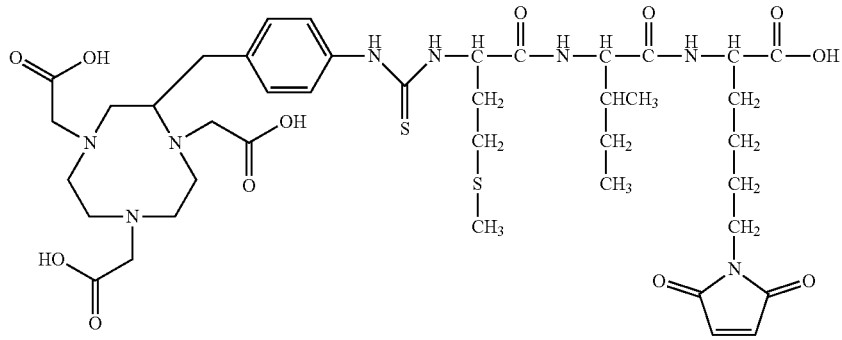

1-4: NOTA-MIK

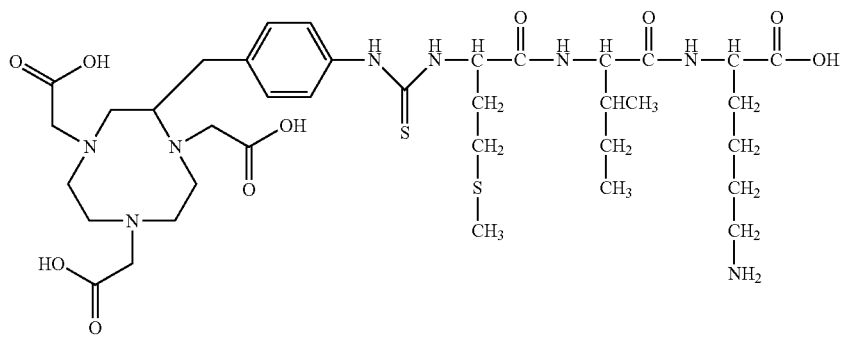

The compound (1), etc. of the present invention may be a pharmacologically allowable salt of the aforementioned compound.

Examples of the pharmacologically allowable salt include an acid addition salt and a base addition salt.

The acid addition salt may be any of an inorganic acid salt and an organic acid salt.

Examples of the inorganic acid salt include a hydrochloride salt, a hydrobromide salt, a sulfate salt, a hydroiodide salt, a nitrate salt, and a phosphate salt.

Examples of the organic acid salt include a citrate salt, an oxalate salt, an acetate salt, a formate salt, a propionate salt, a benzoate salt, a trifluoroacetate salt, a maleate salt, a tartrate salt, a methanesulfonate salt, a benzenesulfonate salt, and a p-toluenesulfonate salt.

The base addition salt may be any of an inorganic base salt and an organic base salt.

Examples of the inorganic base salt include a sodium salt, a potassium salt, a calcium salt, a magnesium salt, and an ammonium salt.

Examples of the organic base salt include a triethylammonium salt, a triethanolammonium salt, a pyridinium salt, and a diisopropylammonium salt.

<Compound (2), etc.>

The compound (2), etc. is a conjugate or a pharmacologically allowable salt thereof, containing the compound (1) or a pharmacologically allowable salt thereof and a target molecule recognition element bonded thereto. The target molecule recognition element may be bonded to the compound (1) or a pharmacologically allowable salt thereof via a linking group or directly. Examples of the linking group include iminothiol derived from 2-iminothiolane.

[Target Molecule Recognition Element]

The "target molecule recognition element" is a molecule, a substituent, or an atomic group that is capable of recognizing a target molecule, for example, capable of being bound to a target molecule, in a living body.

Examples of the target molecule recognition element include a polypeptide, and also include a ligand capable of being bound to the target molecule.

The polypeptide is generally a polypeptide capable of being bound to the target molecule, and preferably a polypeptide capable of being bonded specifically to the target molecule. The polypeptide capable of being bonded specifically to the target molecule means a polypeptide that is capable of being bound to the target molecule, but is not capable of being boded to a molecule other than the target molecule or is capable of being bonded merely weakly thereto.

The target molecule means a molecule that is present in a target site, such as a tissue or a cell, to be an objective for a diagnosis with the radiolabeled drug, and preferably a molecule that is expressed specifically in the target site. The term "expressed specifically" means that the molecule is expressed in the target site, but is not expressed in a site other than the target site or is expressed merely lowly therein.

Examples of the target molecule recognition element include a ligand capable of being bound to a protein that is highly expressed in tissue construction associated with inflammation, tumor cell invasion, or the like, or bound to a protein that is expressed specifically in a tumor cell, and also include an antibody and an antigen binding region fragment of an antibody.

Examples of the antibody include a monoclonal antibody, such as an anti-CD25 antibody and an anti-CD20 antibody.

Examples of the antigen binding region fragment of an antibody include an Fab fragment (which may be hereinafter referred simply to as an "Fab"), an F(ab')$_2$ fragment, an F(ab)$_2$ fragment, and a variable region fragment (which may be hereinafter referred to as an "Fv fragment").

The Fab fragment means a product on the N-terminal side of papain digestion of an antibody, and a fragment having the same domain structure.

The F(ab')₂ fragment means a fragment obtained through reduction of a disulfide bond in a hinge region of F(ab')₂ of an antibody, and a fragment having the same domain structure.

The F(ab)₂ fragment means a dimer containing Fab fragments of two molecules bonded to each other via a disulfide bond.

The Fv fragment is a minimum fragment of an antibody that has a binding activity to an antigen.

More specific examples of the antigen binding region fragment of an antibody include an antibody against a protein that is expressed specifically in a particular cancer cell, and an Fab fragment and an Fv fragment thereof.

Examples of the target molecule recognition element also include a cyclic pentapeptide that is highly expressed in a new blood vessel of tumor and has affinity to integrin, such as cyclo-Arg-Gly-Asp-D-Phe-Lys (which may be hereinafter referred to as "c(RGDfK)". Examples thereof further include bisphosphonic acid, oligo-aspartic acid, and oligo-glutamic acid having affinity to hydroxyapatite present in a large amount in osteoblastic tumor (bone metastases), fMet-Leu-Phe (fMLP), which is a peptide having affinity to a receptor for a scanning factor present on the surface of a macrophage, and folic acid and a derivative thereof capable of being bound to a folic acid receptor, the expression of which is found in a cancer cell.

The target molecule recognition element is not limited to the polypeptides exemplified herein, and any polypeptide that is capable of being bound to a target molecule may be used.

The target molecule recognition element may be bonded by introducing a linking group capable of reacting with the functional group of the compound by using, for example, a thiolation reagent, such as 2-iminothiolane. The linking group may be introduced to an Fab fragment by reacting with the thiolation reagent under a condition of pH 7 to 9, thereby adding a sulfhydryl group to the amino group of the Fab fragment.

The target molecule recognition element used may be a ligand having an Asn-urea-Lys site or a Glu-urea-Lys site. The ligand is selectively bound to a receptor for a prostate specific membrane antigen, the expression of which is significantly increased in prostate cancer.

The Asn-urea-Lys site is a site represented by the following formula:

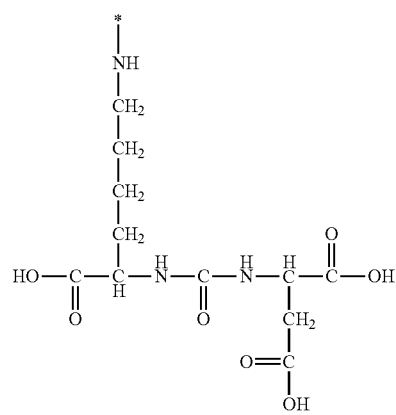 [SMILES: *NCCCCC(NC(=O)NC(CC(=O)O)C(=O)O)C(=O)O]

wherein * represents a bonding site.

The Glu-urea-Lys site is a site represented by the following formula:

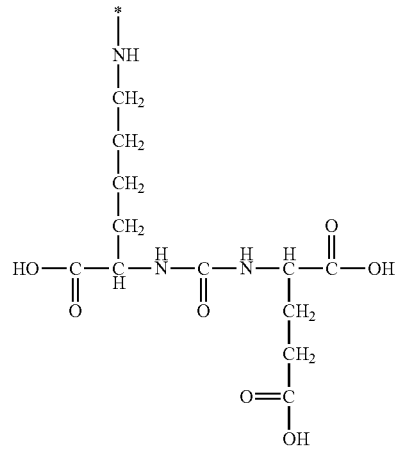 [SMILES: *NCCCCC(NC(=O)NC(CCC(=O)O)C(=O)O)C(=O)O]

wherein * represents a bonding site.

By using the compound (2) of the present invention, a drug for preparing a radiolabeled drug, containing the compound can be produced.

The drug for preparing a radiolabeled drug may contain a pH modifier, such as an aqueous buffer solution, a stabilizer, such as ascorbic acid and p-aminobenzoic acid, and the like, in addition to the compound.

Examples of the compound (2) of the present invention include a compound represented by the following formula (2):

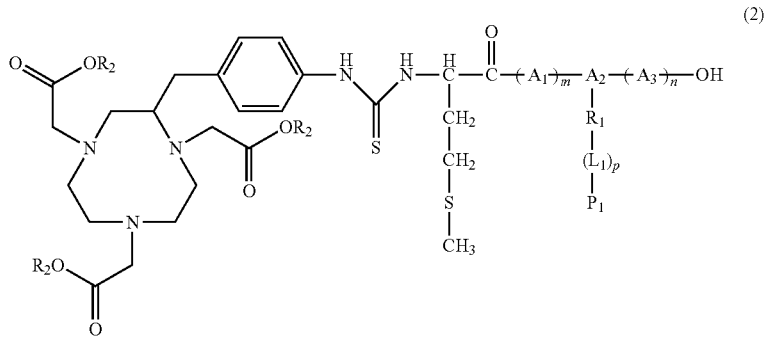

(2)

wherein $A_1$, m, $A_2$, $A_3$, n, $R_1$, and $R_2$ have the same meanings as in the formula (1), $L_1$ represents a linking group linking $R_1$ and $P_1$, p represents 0 or 1, and $P_1$ represents a target molecule recognition element.

$L_1$ forms a bond with a functional group capable of being bonded to the linking group of $R_1$, and also forms a bond with the target molecule recognition element. $L_1$ is preferably iminothiol derived from 2-iminothiolane.

p is preferably 1.

$P_1$ is, for example, the aforementioned target molecule recognition element, and preferably a polypeptide, or a ligand capable of being bound to a target molecule.

<Metal Complex Compound (3), Etc.>

The metal complex compound or a pharmacologically allowable salt thereof (which may be hereinafter referred to as a "metal complex compound (3), etc.") contains one kind of a metal selected from a radioactive metal and a radioactive atom-labeled metal, and the compound or a pharmacologically allowable salt thereof of the present invention, which is coordinated to the metal.

A radiolabeled drug containing the metal complex compound (3), etc. of the present invention may contain an unreacted material and impurities, in addition to the metal complex compound (3), etc., and may contain the metal complex compound (3), etc. that has been purified by a high-pressure liquid chromatography (HPLC) method or the like after the production thereof.

The term "complex" herein means a substance having a ligand coordinated to an atom or an ion of a metal or a metal-like element as the center, and is also referred to as a coordination compound. The coordination means that a ligand forms a coordination bond to the central metal and is arranged around the central metal. The complex is formed with a coordination bond between a ligand and a metal. The formation of a complex with a ligand and a metal may be referred to as complex formation. The coordination bond means a bond having two valence electrons involved in one bond that are supplied only from one atom.

[Metal]

Examples of the metal include $^{62}$Cu, $^{64}$Cu, $^{67}$Cu, $^{67}$Ga, $^{68}$Ga, and $^{18}$F—Al.

$^{18}$F—Al is Al labeled with $^{18}$F, and can be introduced to the compound (2), etc., for example, by the method described in Bioconjugate Chem., 2014, 25, 2038-2045.

The metal is preferably at least one kind selected from the group consisting of $^{67}$Ga, $^{68}$Ga, $^{18}$F—Al, $^{64}$Cu, and $^{67}$Cu, more preferably at least one kind selected from the group consisting of $^{67}$Ga, $^{68}$Ga, and $^{18}$F—Al, and further preferably at least one kind selected from the group consisting of $^{67}$Ga and $^{68}$Ga.

The metal is not limited to these specific examples, and any kind thereof may be used that has a radioactive ray, a radiation dose, and a half-life period that are appropriate for such purposes as a diagnosis using a radiolabeled drug. A short-half-life radioactive isotope of a metal is preferably used from the standpoint of the reduction of the influence on normal tissues and cells in a radiological imaging diagnosis.

The metal complex compound (3), etc. can be produced by forming a complex in vitro by using the aforementioned compound having bonded thereto a target molecule recognition element as a ligand, with a radioactive isotope of a metal. The complex formation may be performed by a simple operation utilizing the known complex forming reaction.

The metal complex compound (3), etc. of the present invention is:

preferably a metal complex compound, etc. containing one kind of a metal selected from a radioactive metal and a radioactive atom-labeled metal; and a compound containing the compound represented by the formula (1), etc. and a target molecule recognition element bonded thereto, and being coordinated to the metal, more preferably a metal complex compound, etc. containing one kind of a metal selected from the group consisting of $^{67}$Ga, $^{68}$Ga, $^{18}$F—Al, $^{64}$Cu, and $^{67}$Cu; and a compound containing the compound represented by the formula (1), etc. and a target molecule recognition element bonded thereto, and being coordinated to the metal, further preferably a metal complex compound, etc. containing one kind of a metal selected from the group consisting of $^{67}$Ga, $^{68}$Ga, $^{18}$F—Al, $^{64}$Cu, and $^{67}$Cu; and a compound containing the compound represented by the formula (1a), etc. and a target molecule recognition element bonded thereto, and being coordinated to the metal, and still further preferably a metal complex compound, etc. containing one kind of a metal selected from the group consisting of $^{67}$Ga, $^{68}$Ga, $^{18}$F—Al, $^{64}$Cu, and $^{67}$Cu; and a compound containing the compound represented by the formula (1a), etc. and a protein or others, e.g., a ligand capable of being bound to a target molecule, which is bonded thereto, and being coordinated to the metal.

In the compounds, the metal is preferably one kind selected from the group consisting of $^{67}$Ga and $^{68}$Ga.

Examples of the metal complex compound (3) include compounds represented by the following formulae (3-1) and (3-2):

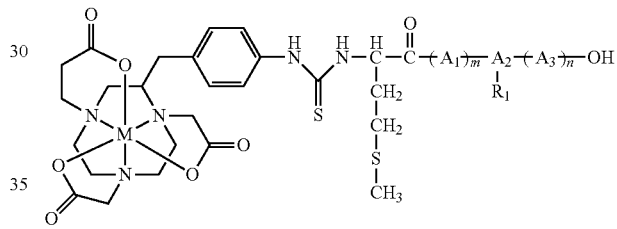

(3-1)

wherein $A_1$, m, $A_2$, $A_3$, n, and $R_1$ have the same meanings as in the formula (1), and M represents $^{62}$Cu, $^{64}$Cu, $^{67}$Cu, $^{67}$Ga, $^{68}$Ga, or $^{18}$F—Al,

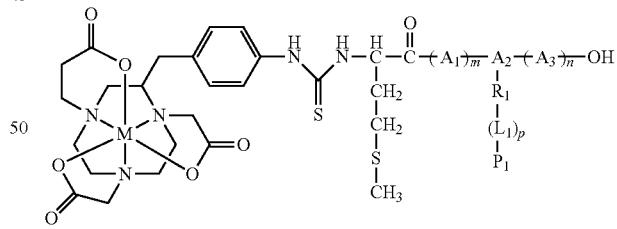

(3-2)

wherein $A_1$, m, $A_2$, $A_3$, n, and $R_1$ have the same meanings as in the formula (1), $L_1$, p, and $P_1$ have the same meanings as in the formula (2), and M represents $^{62}$Cu, $^{64}$Cu, $^{67}$Cu, $^{67}$Ga, $^{68}$Ga, or $^{18}$F—Al, The radiolabeled drug of the present invention may contain the radiolabeled polypeptide as an active ingredient, and may also be prepared as a drug composition containing one kind or two or more kinds of a pharmaceutically allowable carrier (drug carrier) depending on necessity. Examples of the drug carrier include a pH modifier, such as an aqueous buffer solution, an acid, and a base, a stabilizer, such as ascorbic acid and p-aminobenzoic acid, a vehicle, such as D-mannitol, a tonicity agent, and a preservative. A compound that contributes to the improvement of the radiochemical purity may also be added, such as citric acid, tartaric acid, malonic acid, sodium gluconate, and sodium glucoheptonate. The radiolabeled drug of the present invention may be supplied in any form of an aqueous solution, a frozen solution, and a freeze-dried product.

The kit of the present invention contains the aforementioned compound and the aforementioned drug containing the metal, as discrete package units.

Examples of the kit of the present invention include a kit containing, as discrete package units, the compound (1), etc., a drug containing the target molecule recognition element, and a drug containing one kind of a metal selected from a radioactive metal and a radioactive atom-labeled metal; and a kit containing, as discrete package units, the compound (2) containing the compound (1), etc. and the target molecule recognition element bonded thereto, and a drug containing one kind of a metal selected from a radioactive metal and a radioactive atom-labeled metal.

The compounds and the drugs contained in the kits each may contain one kind or two or more kinds of a pharmaceutically allowable carrier (drug carrier) described above depending on necessity.

[Production Method]

The compound (1), etc. and the compound (2), etc. containing the compound (1), etc. and the target molecule recognition element bonded thereto may be synthesized by using a known method, and can be produced, for example, by the method described in the examples in the description herein.

The metal complex compound (3), etc. of the present invention can be produced by forming a complex in vitro by using the compound (2), etc. as a ligand, with a radioactive isotope of a metal. The complex formation may be performed by a known method.

[Administration and Dosage]

The metal complex compound, etc. of the present invention may be used, for example, as a radiolabeled drug used for a radiological imaging diagnosis.

Examples of the radiological imaging diagnosis include single photon emission computed tomography (which may be hereinafter referred simply to as "SPECT") and positron emission tomography (which may be hereinafter referred simply to as "PET").

The diagnosis is not particularly limited, and the compound, etc. may be used for a radiological imaging diagnosis of tumor, inflammation, infection, cardiovascular disease, various diseases of the central nervous system and the like, and organs and tissues, and preferably used for a radiological imaging diagnosis of cancer.

The target molecule recognition element may be selected depending on the characteristics of the target as the objective for the diagnosis, thereby enabling diagnoses and therapies of a wide variety of targets, and thus the radiolabeled drug of the present invention can be widely applied to the field of diagnosis.

Examples of the route of administration of the radiolabeled drug of the present invention include parenteral administration, such as intravenous administration and intraarterial administration, and oral administration, and intravenous administration is preferred.

The route of administration is not limited thereto, any route may be utilized, as far as the function of the radiolabeled drug is effectively expressed after the administration thereof.

The radioactive intensity of the radiolabeled drug of the present invention may be an arbitrary intensity, as far as the intensity is capable of achieving the object by the administration of the drug, and is a clinical dosage that lowers the radiological exposure of the subject as low as possible.

The radioactive intensity may be determined with reference to the radioactive intensities used in the general diagnostic methods and therapy methods using a radiolabeled drug. The dosage thereof may be determined as a dosage providing radioactivity capable of enabling the imaging, in consideration of various conditions including the age and the weight of the subject, the suitable radiological imaging instrument, the condition of the objective disease, and the like.

In the case of a human as the subject, the amounts of radioactivity for the metals are as follows.

In the case where $^{67}$Ga is used, the application to SPECT is generally assumed, and the dosage of the diagnostic agent is not particularly limited, and for example, may be from 1.1 MBq/kg to 1.5 MBq/kg in terms of amount of radioactivity of $^{67}$Ga.

In the case where $^{68}$Ga is used, the application to PET is generally assumed, and the dosage of the diagnostic agent may be from 1.5 MBq/kg to 3 MBq/kg in terms of amount of radioactivity of $^{68}$Ga.

In the case where $^{64}$F—Al is used, the application to PET is generally assumed, and the dosage of the diagnostic agent may be from 1.5 MBq/kg to 4 MBq/kg in terms of amount of radioactivity of $^{18}$F.

In the case where $^{64}$Cu is used, the application to PET and radiation therapy is generally assumed, and the dosage of the diagnostic agent may be from 1.5 MBq/kg to 4 MBq/kg in terms of amount of radioactivity of $^{64}$Cu, and may be from 0.93 GBq/m$^2$ to 2.22 GBq/m$^2$ in terms of amount of radioactivity for radiation therapy.

In the case where $^{67}$Cu is used, the application to radiation therapy is generally assumed, and the dosage of the diagnostic agent may be from 0.93 GBq/m$^2$ to 2.22 GBq/m$^2$ in terms of amount of radioactivity of $^{67}$Cu.

According to the present invention, as described above, a compound, etc. capable of providing a radiolabeled drug that can reduce the renal accumulation thereof in the early stage after the administration thereof can be provided. The radiolabeled drug of the present invention provides a definite image as compared to the ordinary ones, and thus enables a radiological imaging diagnosis with high accuracy.

EXAMPLES

The examples described below are provided only for exemplification of the present invention and do not restrict the technical scope of the present invention. The experiments shown below were performed after the authorization by the Animal Ethics Committee of Chiba University.

In Examples and Comparative Examples shown below, the following abbreviations were used for the substituents, the compounds, and the organic solvents.

Fmoc: fluorenylmethoxycarbonyl group
Boc: tert-butoxycarbonyl group
Trt(2-Cl): 2-chlorotrityl group
p-SCN-Bn-NOTA: 2-S-(4-isothiocyanatobenzyl)-1,4,7-triazacyclononane-1,4,7-triacetic acid
Cl-Trt(2-Cl) Resin: 2-chlorotrityl chloride resin Fmoc-Lys(Dde)-OH: N-α-(9-fluorenylmethoxycarbonyl)-N-ε-[1-(4,4-dimethyl-2,6-dioxocyclohexylidene) ethyl]-L-lysine
Fmoc-Lys-OH—HCl: N-α-(9-fluorenylmethoxycarbonyl)-L-lysine hydrochloride
TFA: trifluoroacetic acid
MeCN: acetonitrile
DIPEA: N,N-diisopropylethylamine
DMF: dimethylformamide
DIC: N,N'-diisopropylcarbodiimide
HOBt: 1-hydroxybenzotriazole
NMCM: N-methoxycarbonylmaleimide EDTA: ethylenediamine tetraacetic acid
DPS: 2,2'-dipyridyl disulfide
EtOH: ethanol
FBS: fetal bovine serum
D-PBS: Dulbecco's phosphate buffered saline
EGTA: glycol ether diamine tetraacetate
MGTA: DL-2-mercaptomethyl-3-guanidinoethylthiopropionic acid

[Measurement Methods and Experimental Animals]

In Examples and Comparative Examples shown below, the properties and the like were measured in the following manners.

[NMR (Nuclear Magnetic Resonance)]

The analysis by $^1$H-NMR was performed by using JEOL ECS-400 Spectrometer (produced by JEOL, Ltd.).

[ESI-MS (Electrospray Ionization Mass Spectroscopy)]

The analysis by ESI-MS was performed by using HPLC1200 series-6130 quadrupole LC/MS mass spectrometer (produced by Agilent Technologies, Inc.).

[Thin Layer Chromatography (TLC)]

The analysis by thin layer chromatography (TLC) was performed by using a silica plate (TLC aluminium sheets Silica gel 60 RP-18$F_{254S}$, available from Merck & Co., Inc.) in such a manner that a chromatogram obtained by developing by 10 cm with a developing solvent containing a 0.1 M ammonium acetate aqueous solution and methanol (1/1) was cut into 5 mm fractions, and the fractions each were measured for radioactivity with an auto well gamma system (WIZARD 3, available from Perkin-Elmer Corporation).

[Cellulose Acetate Membrane Electrophoresis (CAE)]

In cellulose acetate membrane electrophoresis (which may be hereinafter referred to as "CAE"), migration was performed at a constant current (1 mA/cm) with a cellulose acetate membrane (Advantec Seleca-V, available from Toyo Roshi Kaisha, Ltd.) cut into 11 cm×1 cm as a migration membrane and a Veronal buffer (pH 8.6, I=0.06) or Solvent 2 (20 mM P.B. (pH 6.0)) as a buffer solution. The cellulose acetate membrane after the migration was cut into 5 mm fractions, and the fractions each were measured for radioactivity with the auto well gamma system.

[Reversed-Phase High Pressure Liquid Chromatography (RP-HPLC) and Size-Exclusion High Pressure Liquid Chromatography (SE-HPLC)]

(Analysis)

The analysis by reversed-phase high pressure liquid chromatography (which may be hereinafter referred to as "RP-HPLC") was performed by using L-7405 (produced by Hitachi, Ltd.) as a UV detector, L-7100 (produced by Hitachi, Ltd.) as a liquid feed pump, and Cosmosil 5C$_{18}$-AR-300 column (4.6×150 mm, available from Nacalai Tesque, Inc.) as an analytical column.

The elution was performed at a flow rate of 1.0 mL/min by the linear gradient method, in which the mobile phases used were 0.1% (v/v) TFA/H$_2$O (phase A) and 0.1% (v/v) TFA/MeCN (phase B), which were changed from phase A 95% (v/v) and phase B 5% (v/v) to phase A 70% (v/v) and phase B 30% (v/v) in the period of from 0 to 20 minutes, and from phase A 70% (v/v) and phase B 30% (v/v) to phase A 0% (v/v) and phase B 100% (v/v) in the period of from 20 to 40 minutes.

(Sampling)

The sampling by RP-HPLC was performed by using Cadenza 5CD-C18 column (20×150 mm, available from Imtakt Corporation) connected to a guard column, Cadenza 5CD-C18 Guard Column (10×8 mm, available from Imtakt Corporation).

The elution was performed at a flow rate of 5.0 mL/min by the linear gradient method, in which the mobile phases used were 0.1% (v/v) TFA/H$_2$O (phase A) and 0.1% (v/v) TFA/MeCN (phase B), which were changed from phase A 90% (v/v) and phase B 10% (v/v) to phase A 20% (v/v) and phase B 80% (v/v) in the period of from 0 to 30 minutes, and from phase A 20% (v/v) and phase B 80% (v/v) to phase A 0% (v/v) and phase B 100% (v/v) in the period of from 30 to 40 minutes.

The analysis by size-exclusion HPLC (which may be hereinafter referred to as "SE-HPLC") was performed by performing the elution at a flow rate of 1.0 mL/min by using a 0.1 M phosphate buffer solution (pH 6.8) as a mobile phase and Cosmosil 5 Diol-300II (7.5×600 mm, available from Nacalai Tesque, Inc.) connected to a guard column, Cosmosil 5 Diol-300II Guard Column (7.5×50 mm, available from Nacalai Tesque, Inc.).

The elute was measured for absorbance at 254 nm for RP-HPLC or 280 nm for SE-HPLC, and the analysis of the $^{67}$Ga-labeled compound was performed in such a manner that a γ-ray detector, Gabi Star (produced by Raytest, Inc.) was connected on-line, or the elute was fractionated with an interval of 0.5 minute with a fraction collector (Frac-920, available from GE Healthcare Japan Corporation) and then analyzed for the radioactivity with the auto well gamma system.

[Experimental Animals]

The experimental animals used were male ddY SPF mice of 6 weeks of age and male BALB/c-nu/nu mice (available from Japan SLC, Inc.).

Synthesis of Ligand

Synthesis Example 1

Synthesis of Compound R1 (NOTA-Bn-Met-OH)

p-SCN-Bn-NOTA (10 mg, 0.022 mmol) was dissolved in a 0.1 M borate buffer solution having pH 9.0 to make a final concentration of from 10 to 100 mg/mL, and controlled to pH 8 to 9 with a 0.1N NaOH aqueous solution, and then L-methionine (4.97 mg, 0.33 mmol) was added thereto, followed by reacting at room temperature for 2 hours. The product was purified by RP-HPLC for fractionation, so as to provide the compound R$_1$ in an amount of 2.5 mg (4.2 μmol, yield: 19%) as a white solid matter.

Compound R1: ESI-MS m/z [M+H]$^+$ 600, Found 600

Example 1

Synthesis of NOTA-MVK(Mal)

The synthesis of NOTA-MVK(Mal) was performed by the following scheme.

Scheme.

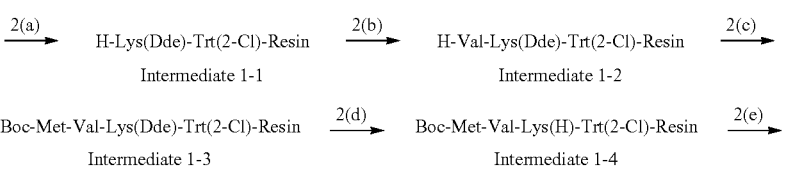

-continued

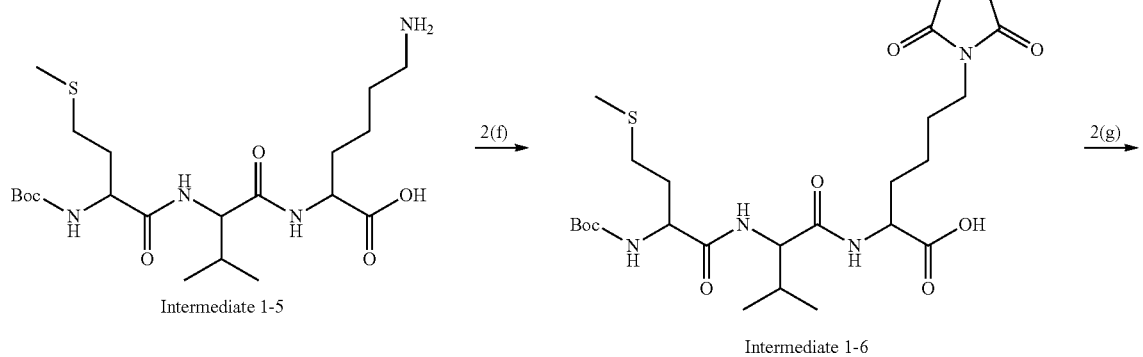

Intermediate 1-5 → 2(f) → Intermediate 1-6 → 2(g) →

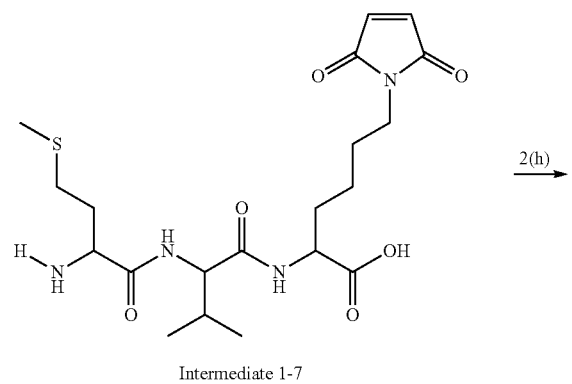

Intermediate 1-7 → 2(h) →

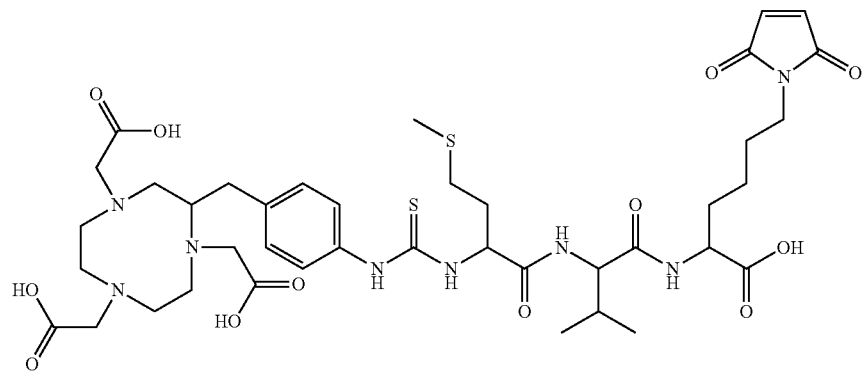

NOTA-Met-Val-Lys(Mal)-OH

2(a) Fmoc-Lys(Dde)-OH; 2(b) Fmoc-Val-OH; 2(c) Boc-Met-OH; 2(d) 2% hydradine/DMF;
2(e) acetic acid:dichloromethane:2,2,2-trifluoroethanol = 3:6:1; 2(f) NMCM; 2(g) 4N HCl/ethylacetate; 2(h) p-SCN-NOTA.

Synthesis Example 2(a)

Synthesis of Intermediate 1-1 (H-Lys(Dde)-Trt(2-Cl Resin)

Cl-Trt(2-Cl) Resin (195 mg, 0.313 mmol, available from Watanabe Chemical Industries, Ltd.), Fmoc-Lys(Dde)-OH (250 mg, 0.469 mmol) and DIPEA (327 µL, 1.876 mmol) were reacted in dichloromethane (2 mL) for 1.5 hours. The reaction was terminated by adding methanol (1 mL) and DIPEA (327 µL, 1.876 mmol) thereto. The resin was rinsed with DMF and then dichloromethane. Subsequently, 20% (v/v) piperidine/DMF (3 mL) was added, and the reaction mixture was stirred at room temperature for 20 minutes, so as to provide an Intermediate 1-1.

A part of the resin was collected and subjected to the Kaiser test (see Analytical Biochemistry, 1970, 34, 595-598) to confirm the deprotection of the $N^\alpha$-Fmoc group. The resin was rinsed with DMF and dichloromethane, and dried, and then the amount of Fmoc-Lys(Dde)-OH introduced to the resin was determined by measuring the absorbance at $A_{301}$ of N-(9-fluorenylmethyl)piperidine formed in the piperidine treatment (0.280 mmol, yield: 89.5%) (see Journal of Organic Chemistry, 2004, 69, 4586-4594).

Synthesis Example 2(b)

Synthesis of Intermediate 1-2 (H-Val-Lys(Dde)-Trt (2-Cl) Resin)

The intermediate 1-1 (0.280 mmol) was stirred with 2.5 equivalents of Fmoc-Val-OH (237 mg, 0.783 mmol), DIC (108 μL, 0.783 mmol), and HOBt (107 mg, 0.783 mmol) in DMF (3 mL) by the Fmoc solid-phase synthesis method at room temperature for 2 hours. A part of the resin was collected and subjected to the Kaiser test to confirm the completion of the condensation reaction, and then the resin was rinsed with DMF. Subsequently, 20% (v/v) piperidine/DMF (3 mL) was added thereto, and the reaction mixture was stirred at room temperature for 20 minutes, so as to provide an Intermediate 1-2. A part of the resin was collected and subjected to the Kaiser test to confirm the deprotection of the $N^\alpha$-Fmoc group.

Synthesis Example 2(c)

Synthesis of Intermediate 1-3 (Boc-Met-Val-Lys (Dde)-Trt(2-Cl) Resin)

The intermediate 1-2 (0.280 mmol) was stirred with 2.5 equivalents of Boc-Met-OH (249 mg, 0.783 mmol), DIC (108 μL, 0.783 mmol), and HOBt (107 mg, 0.783 mmol) in DMF (3 mL) by the Fmoc solid-phase synthesis method at room temperature for 2 hours, so as to produce an intermediate 1-3. A part of the resin was collected and subjected to the Kaiser test to confirm the completion of the condensation reaction, and then the resin was rinsed with DMF and dichloromethane.

Synthesis Example 2(d)

Synthesis of Intermediate 1-4 (Boc-Met-Val-Lys (H)-Trt(2-Cl) Resin)

The intermediate 1-3 (0.280 mmol) was stirred in 2% (v/v) hydrazine/DMF (3 mL) at room temperature for 1 hour, and then the resin was rinsed with DMF and dichloromethane, and then dried under reduced pressure, so as to produce an intermediate 1-4.

Synthesis Example 2(e)

Synthesis of Intermediate 1-5 (Boc-Met-Val-Lys(H)—OH)

The intermediate 1-4 (0.280 mmol) was stirred in a mixed liquid of acetic acid, 2,2,2-trifluoroethanol, and dichloromethane (3/1/6 in volume, 2 mL) at room temperature for 2 hours. The resin was removed by filtration, and then diethyl ether (3 mL) was added to the residue obtained by distillation under reduced pressure of the filtrate, so as to perform crystallization. The crystals were collected by filtration, rinsed with diethyl ether, and dried under reduced pressure, so as to provide an intermediate 1-5 in an amount of 84 mg (0.177 mmol, yield: 63%) as a white solid matter.

Intermediate 1-5: $^1$H-NMR (CD$_3$OD): δ 0.97-0.99 [6H, m, CH$_3$], 1.44 [9H, s, OtBu], 1.65-2.11 [12H, m, CH$_2$, CH, SCH$_3$], 2.48-2.56 [2H, m, CH$_2$NH$_2$], 2.88-2.93 [2H, t, SCH$_2$], 4.15-4.87 [3H, m, CHCO]

ESI-MS m/z [M+H]+477, Found 477.

Synthesis Example 2(f)

Synthesis of Intermediate 1-6 (Boc-Met-Val-Lys(Mal)-OH)

The intermediate 1-5 (6.60 mg, 13.9 μmol) was dissolved in a saturated NaHCO$_3$ aqueous solution (100 μL) under cooling with ice, to which NMCM (3.22 mg, 20.8 μmol was added. After stirring under cooling with ice for 2 hours, the solution was neutralized with a 5% (wt/wt) citric acid solution. The solution was extracted with chloroform (5 mL×3), the extract was dried over sodium sulfate, and the filtrate was distilled under reduced pressure, so as to provide an intermediate 1-6 in an amount of 7.26 mg (13.1 μmol, yield: 94.1%) as a white solid matter.

Intermediate 1-6: $^1$H-NMR (CDCl$_3$): δ 0.90-0.95 [6H, m, CH$_3$], 1.32-1.44 [2H, m, CH$_2$], 1.44 [9H, s, Boc], 1.48-1.70 [2H, m, CH$_2$CH$_2$-maleimide], 1.70-1.92 [1H, m, CH], 1.92-2.10 [2H, m, CH$_2$CHCO], 2.10-2.28 [5H, m, CH$_2$CH$_2$SCH$_3$, SCH$_3$], 2.54 [2H, t, SCH$_2$], 3.48-3.53 [2H, m, CH$_2$-maleimide], 4.05-4.44 [3H, m, CHCO], 6.72 [2H, s, maleimide]

ESI-MS m/z [M+H]+ 557, Found 557.

Synthesis Example 2(g)

Synthesis of Intermediate 1-7 (H-Met-Val-Lys(Mal)-OH)

The intermediate 1-6 (7.26 mg, 13.1 μmol) was dissolved in 4 N HCl/ethyl acetate, and the solution was stirred at room temperature for 1 hour. The solvent was distilled off under reduced pressure, and the residue was subjected to azeotropy with hexane, so as to provide 5.92 mg of a hydrochloride of an intermediate 1-7 (12.1 μmol, yield: 92.4%) as a white solid matter.

Intermediate 1-7: ESI-MS m/z [M+H]+ 457, Found 457.

Synthesis Example 2(h)

Synthesis of Compound 1-1 (NOTA-Met-Val-Lys(Mal)-OH)

The hydrochloride of the intermediate 1-7 (5 mg, 10.2 μmol) was dissolved in dried DMF (100 μL), to which triethylamine (6 μL) was added. p-SCN-Bn-NOTA (7.4 mg, 16.4 μmol) was added thereto, and the mixture was stirred at room temperature for 2 hours, then diluted 10 times with H$_2$O, and purified by RP-HPLC for fractionation, so as to provide a compound 1-1 (which may be hereinafter referred to as "NOTA-MVK(mal)") in an amount of 2.8 mg (3.1 μmol, yield: 28.2%) as a white solid matter.

Compound 1-1: $^1$H-NMR (D$_2$O): 0.90-0.95 [6H, m, CH$_3$], 1.28-1.30 [2H, m, CH$_2$], 1.52-1.56 [2H, m, CH$_2$CH$_2$-maleimide], 1.75-1.86 [2H, m, CH$_2$CHCO], 2.04-2.10 [6H, m, CH, CH$_2$CH$_2$SCH$_3$, SCH$_3$], 2.50-2.57 [2H, m, SCH2], 2.57-3.88 [21H, m, CH$_2$-maleimide, CH$_2$, CH, CH$_2$COOH], 4.13-4.25 [3H, m, CHCO], 6.78 [2H, s, maleimide], 7.26-7.34 [4H, m, phenyl]

ESI-MS m/z [M+H]+ 907, Found 907.

HRMS m/z [M+H]+ calculated for C$_{40}$H$_{59}$N$_8$O$_{12}$S$_2$ 907.36938, observed 907.36338.

Reference Example 1

Synthesis of NOTA-MVK(Bzo)

The synthesis of NOTA-MVK(Bzo) was performed by the following scheme.

Scheme.

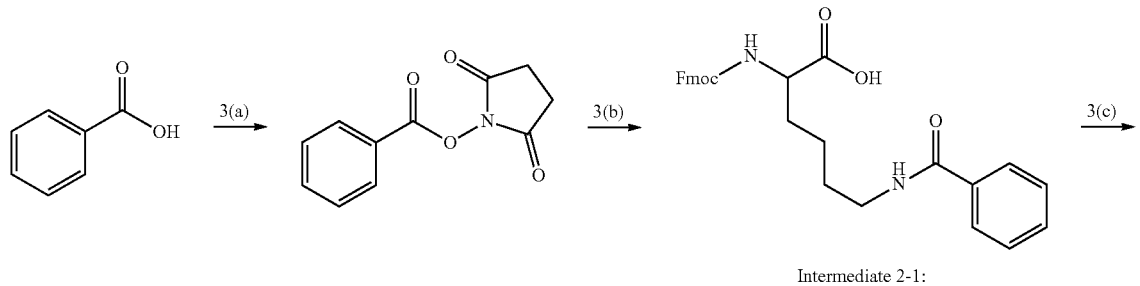

Intermediate 2-1:
Fmoc-Lys(Bzo)-OH

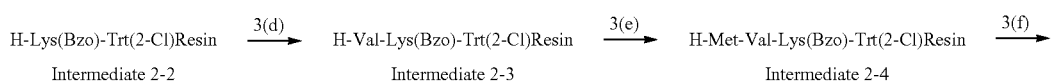

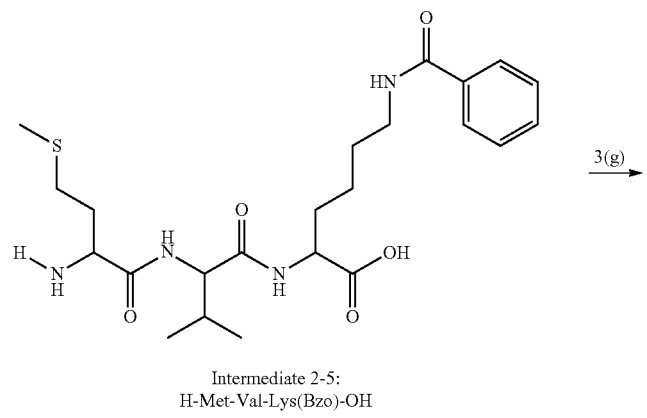

Intermediate 2-5:
H-Met-Val-Lys(Bzo)-OH

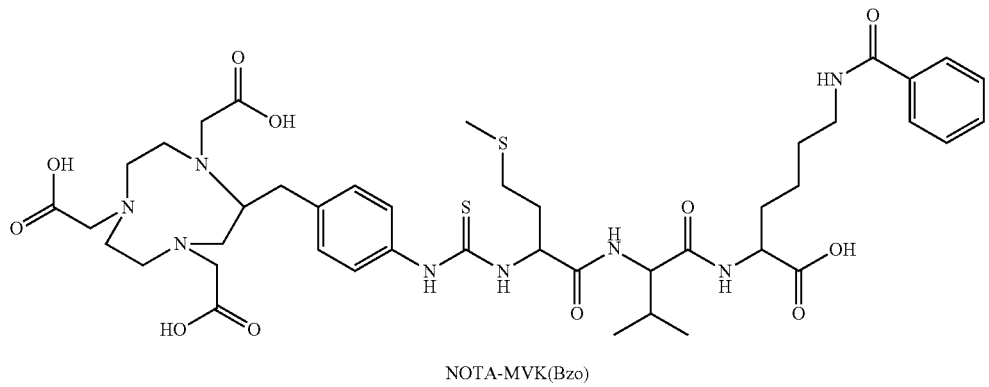

NOTA-MVK(Bzo)

Synthesis Example 3(a)

Synthesis of N-(Benzoyloxy)succinimide

Benzoic acid (1 g, 8.20 mmol) and N-hydroxysuccinimide (1.04 g, 9.02 mmol) were dissolved in 30 mL of dried DMF, to which dicyclohexylcarbodiimide (1.86 g, 9.02 mmol) having been dissolved in 10 mL of dried DMF was added dropwise in an argon atmosphere at 0° C. The mixture was returned to room temperature, and then stirred for 12 hours, the precipitate was removed by filtration, and the solvent was distilled off under reduced pressure, so as to provide 2.06 g of a crude product of N-(benzoyloxy)succinimide as a white solid matter. The compound contained a small amount of urea, but was used for the subsequent reaction.

$^1$H-NMR (CDCl$_3$): δ 2.91 (4H, t, C$\underline{H}_2$), 8.00-8.24 (5H, m, Ar—$\underline{H}$)

ESI-MS m/z [M+H]$^+$ 220, Found 220.

Synthesis Example 3(b)

Synthesis of Intermediate 2-1 Fmoc-Lys(Bzo)-OH

N-(Benzoyloxy)succinimide (27 mg, 0.12 mmol) was dissolved in dichloromethane (1 mL), and added dropwise to Fmoc-Lys-OH.HCl (50 mg, 0.12 mmol) and sodium hydrogen carbonate (20 mg, 0.12 mmol) having been dissolved in MilliQ (1 mL), and the mixture was vigorously stirred at room temperature. After stirring for 24 hours, the mixture was acidified with 1 N hydrochloric acid, and then extracted with dichloromethane (5 ml×3), and the organic layer was dried over anhydrous magnesium sulfate. After distilling off the solvent under reduced pressure, the residue was purified by open column chromatography with hexane/ethyl acetate/acetic acid=1/2/0.1 as an elution solvent, so as to provide an intermediate 2-1 (Fmoc-Lys(Bzo)-OH) in an amount of 57 mg (0.12 mmol, 49%).

$^1$H-NMR (CDCl$_3$): δ 1.48-1.94 (6H, m, C$\underline{H}_2$), 3.46 (2H, t, C$\underline{H}_2$), 3.73-4.40 (4H, m, C$\underline{H}$, C$\underline{H}_2$), 7.23-8.06 (13H, m, Ar—$\underline{H}$)

ESI-MS m/z [M+H]$^+$ 473, Found 473.

Synthesis Example 3(c)

Synthesis of Intermediate 2-2H-Lys(Bzo)-Trt(2-Cl) Resin

Cl-Trt(2-Cl) Resin (32 mg, 0.052 mmol, available from Watanabe Chemical Industries, Ltd.), Fmoc-Lys(Bzo)-OH (37 mg, 0.078 mmol), and DIPEA (36 µL, 0.209 mmol) were reacted in dichloromethane (0.5 mL) for 1.5 hours. The reaction was terminated by adding methanol (0.2 mL) and DIPEA (36 µL, 0.209 mmol) thereto. The resin was rinsed with DMF and then dichloromethane. Subsequently, 20% (v/v) piperidine/DMF (3 mL) was added, and the reaction mixture was stirred at room temperature for 20 minutes, so as to provide an Intermediate 2-2 (H-Lys(Bzo)-Trt(2-Cl) Resin). A part of the resin was collected and subjected to the Kaiser test to confirm the deprotection of the N$^\alpha$-Fmoc group. The resin was rinsed with DMF and dichloromethane, and dried, and then the amount of Fmoc-Lys(Bzo)-OH introduced to the resin was determined by measuring the absorbance at A$_{301}$ of N(9-fluorenylmethyl)piperidine formed in the piperidine treatment (0.040 mmol, 76%).

Synthesis Example 3(d)

Synthesis of Intermediate 2-3H-Val-Lys(Bzo)-Trt(2-Cl) Resin

H-Lys(Bzo)-Trt(2-Cl)Resin (0.026 mmol) was stirred with 2.5 equivalents of Fmoc-Val-OH (22 mg, 0.065 mmol), N,N'-diisopropylcarbodiimide (DIC, 10 µL, 0.065 mmol), and 1-hydroxybenzotriazole (HOBt, 10 mg, 0.065 mmol) in DMF (3 mL) by the Fmoc solid-phase synthesis method at room temperature for 2 hours. A part of the resin was collected and subjected to the Kaiser test to confirm the completion of the condensation reaction, and then the resin was rinsed with DMF. Subsequently, 20% (v/v) piperidine/DMF (3 mL) was added thereto, and the reaction mixture was stirred at room temperature for 20 minutes, so as to provide an Intermediate 2-3 (H-Val-Lys(Bzo)-Trt(2-Cl) Resin). A part of the resin was collected and subjected to the Kaiser test to confirm the deprotection of the N$^\alpha$-Fmoc group.

Synthesis Example 3(e)

Synthesis of Intermediate 2-4H-Met-Val-Lys(Bzo)-Trt(2-Cl) Resin

H-Val-Lys(Bzo)-Trt(2-Cl)Resin (0.026 mmol) as a starting material was stirred with 2.5 equivalents of Fmoc-Met-OH (24 mg, 0.065 mmol), N,N'-diisopropylcarbodiimide (10 µL, 0.065 mmol), and HOBt (9.9 mg, 0.065 mmol) in DMF (1 mL) by the Fmoc solid-phase synthesis method at room temperature for 2 hours. A part of the resin was collected and subjected to the Kaiser test to confirm the completion of the condensation reaction, and then 20% piperidine/DMF (3 mL) was added, and the reaction mixture was stirred at room temperature for 20 minutes, so as to provide an intermediate 2-4 (H-Met-Val-Lys(Bzo)-Trt(2-Cl) Resin). A part of the resin was collected and subjected to the Kaiser test to confirm the deprotection of the N$^\alpha$-Fmoc group.

Synthesis Example 3(f)

Synthesis of Intermediate 2-5H-Met-Val-Lys(Bzo)-OH

H-Met-Val-Lys(Bzo)-Trt(2-Cl) Resin was stirred in a mixed liquid of acetic acid, 2,2,2-trifluoroethanol, and dichloromethane (3/1/6 in volume, 2 mL) at room temperature for 2 hours. The resin was removed by filtration, and then diethyl ether (3 mL) was added to the residue obtained by distillation under reduced pressure of the filtrate, so as to perform crystallization. The crystals were collected by filtration, rinsed with diethyl ether, and dried under reduced pressure, so as to provide an acetate salt of an intermediate 2-4 (H-MetValLys(Bzo)-OH) (9.7 mg, 69.0%) as a white solid matter.

$^1$H-NMR (D$_2$O): δ 0.90-0.92 (6H, m, C$\underline{H}_3$), 1.37-1.88 (6H, m, C$\underline{H}_2$), 1.97-2.06 (6H, m, SC$\underline{H}_3$, COCHC$\underline{H}$, SC$\underline{H}_2$C$\underline{H}_2$), 2.44-2.49 (2H, m, SC$\underline{H}_2$), 3.30-3.38 (2H, m, NHC$\underline{H}_2$), 4.04-4.17 (3H, m, COC$\underline{H}$), 7.48-7.73 (5H, m, Ar—$\underline{H}$)

ESI-MS m/z [M+H]$^+$ 481, Found 481.

m.p.: 179-180° C.

Synthesis Example 3(g)

Synthesis of NOTA-MVK(Bzo)

p-SCN-Bn-NOTA (5.6 mg, 12.5 µmol) was dissolved in a 0.1 M borate buffer solution having pH 9.0 to make a final concentration of from 10 to 100 mg/mL, and controlled to pH 8 to 9 with a 0.1N NaOH aqueous solution, and then H-MetValLys(Bzo)-OH (4.0 mg, 8.3 µmol) was added thereto, followed by reacting at room temperature for 2 hours. The product was purified by RP-HPLC for fractionation, so as to provide NOTA-MVK(Bzo) shown by the following formula in an amount of 2.5 mg (2.69 µmol, 32.4%) as a white solid matter.

$^1$H-NMR (DMSO-d6): δ 0.85-0.90 (6H, m, C$\underline{H}_3$), 1.23-1.68 (6H, m, C$\underline{H}_2$), 1.98-2.10 (6H, m SC$\underline{H}_3$, COCHC$\underline{H}$, SC$\underline{H}_2$C$\underline{H}_2$), 2.41-4.28 (26H, m, C$\underline{H}_2$, C$\underline{H}$, SC$\underline{H}_2$, COC$\underline{H}$), 7.43-8.16 (9H, m, Ar—$\underline{H}$)

ESI-MS m/z [M+H]$^+$ 931, Found 931.

HRMS m/z [M+H]$^+$ calculated for C$_{43}$H$_{63}$N$_8$O$_{11}$S$_2$ 931.40577, observed 931.41015.

m.p.: 146-148° C.

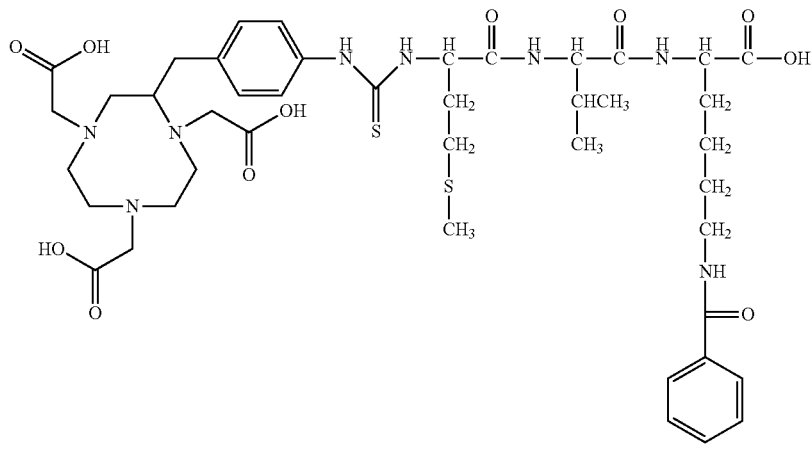

NOTA-MVK(Bzo)

Reference Example 2

Synthesis of NOTA-MIK(Bzo)

NOTA-MIK(Bzo) shown by the following formula was synthesized in the same manner as in Reference Example 1 except that Fmoc-Ile-OH was used instead of Fmoc-Val-OH in Synthesis Example 2(b).

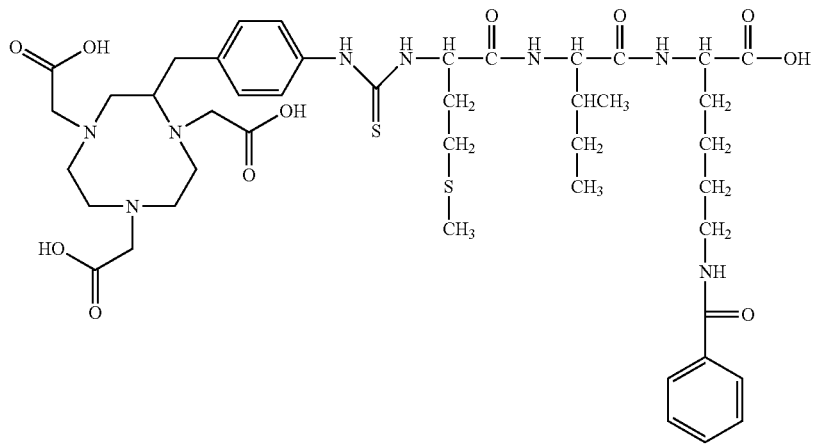

NOTA-MIK(Bzo)

Production of Bifunctional Chelate Reagent-Bonded Fab

Synthesis Example 4-1: Production of Fab

C-kit (9 mg, 12A8, available from Immuno-Biological Laboratories Co., Ltd.) was dissolved in a 20 mM phosphate buffer solution (pH 7.0, 1.5 mL) containing 10 mM Na$_2$EDTA and 20 mM cysteine, to which 500 μL of an immobilized papain 50% slurry (available from Thermo Fisher Scientific, Inc.) was added, and the mixture was incubated at 37° C. for 42 hours. After completing the reaction, 2 mL of a 10 mM tris hydrochloride buffer solution (Tris-HCl) (pH 7.5) was added thereto, the mixture was filtered with a filter of 0.45 μm, and the filtrate was recovered. The filtrate was replaced with a 20 mM phosphate buffer solution (pH 7.0) by using a 10 kDa ultrafiltration membrane, and concentrated to 1 mL. Thereafter, the concentrated filtrate was purified with Protein A column, so as to provide Fab. The resulting Fab was confirmed for the formation thereof by SE-HPLC eluting with a 0.1 M phosphate buffer solution (pH 6.8) at a flow rate of 1.0 mL/min, and measured for the concentration thereof by measuring A280.

Synthesis Example 4-2: Production of IT-Fab

An Fab solution (200 μL, 2.0 mg/mL) was prepared by using a sufficiently deaerated 0.16 M borate buffer solution (pH 8.0) containing 2 mM EDTA, to which 2-iminothiolane (2-IT) (7.5 μL, 2.0 mg/mL) having been dissolved in the same buffer solution was added and reacted at 37° C. for 30 minutes. After completing the reaction, the excess 2-IT in the reaction solution was removed by the spin column method using Sephadex G-50 Fine having been equilibrated with a sufficiently deaerated 0.1 M phosphate buffer solution (pH 6.0) containing 2 mM EDTA (see Analytical Biochemistry, 1984, 142, 68-78). The number of thiol groups introduced to one molecule of Fab was measured with 2,2'-dipyridyldisulfide (DPS) (see Archives of Biochemistry and Biophysics, 1967, 119, 41-49).

[Production of Ligand Having Fab Bonded Thereto]

Example 2

Production of NOTA-MVK-Fab 1.25 μL of NOTA-MVK(mal) having been dissolved in DMF (50 mg/mL) was added to the Fab solution thiolated with 2-IT (100 μL) and reacted at 37° C. for 1 hour. Subsequently, an iodoacetamide solution (10 mg/mL) was prepared by using a 0.1 M phosphate buffer solution (pH 6.0), 12.5 μL of which was added, and the reaction was performed at 37° C. for 1 hour, so as to alkylate unreacted thiol groups. Thereafter, the product was purified by the spin column method using Sephadex G-50 Fine having been equilibrated with a 0.25 M acetate buffer solution (pH 5.5), so as to provide a compound 2-1 (which may be hereinafter referred to as "NOTA-MVK-Fab") shown by the following formula. The number of units derived from NOTA-MVK (mal) introduced to one molecule of Fab was obtained by subtracting the thiol number measured with DPS before adding iodoacetamide (see Archives of Biochemistry and Biophysics, 1967, 119, 41-49) from the thiol number obtained above.

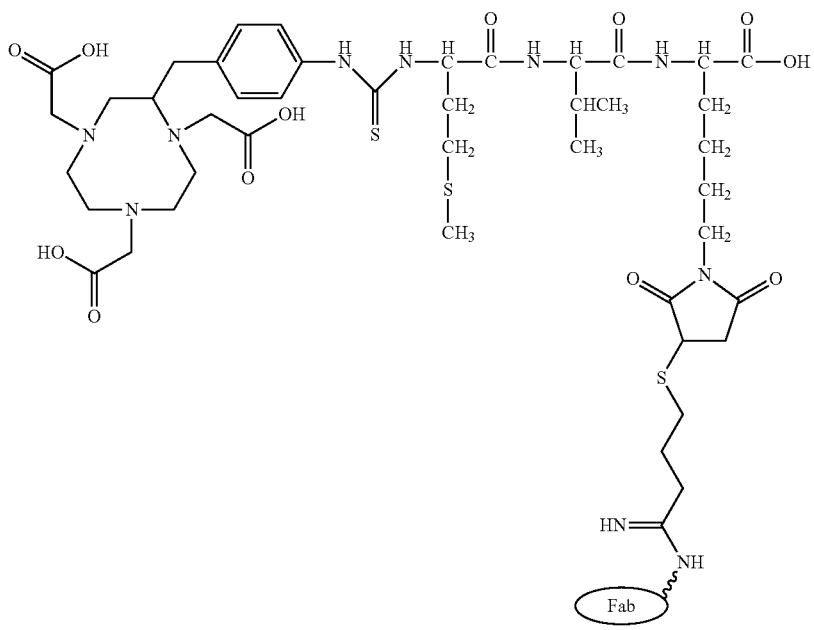

2-1: NOTA-MVK-Fab

Comparative Example 1

Production of NOTA-MI-Fab

NOTA-MI-Fab was produced in the same manner as in Example 1 except that NOTA-MVK(mal) was changed to NOTA-MI(mal) (prepared according to the method described in Bioconjugate Chem., 2014, 25, 2038-2045).

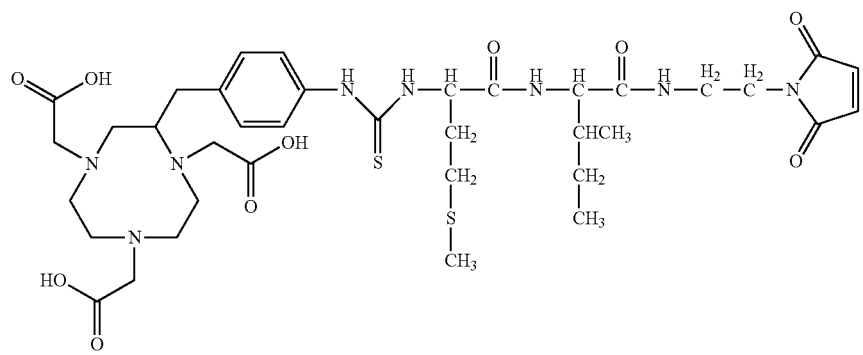

NOTA-MI(Mal)

Comparative Example 2

Production of NOTA-SCN-Fab

An Fab solution (100 μL, 5.0 mg/mL) was prepared by using a 0.1 M borate buffer solution (pH 9.0), to which 2.25 μL of p-SCN-Bn-NOTA having been dissolved in a 0.1 M borate buffer solution (pH 9.0) (5.0 mg/mL) was added, and the mixture was stirred at room temperature for 12 hours. After completing the reaction, the product was purified by the spin column method using Sephadex G-50 Fine having been equilibrated with a sufficiently deaerated 0.25 M acetate buffer solution (pH 5.5), so as to provide NOTA-SCN-Fab.

[Production of Radioactive Metal-Labeled Fab]

Example 3

Production of $^{67}$Ga-NOTA-MVK-Fab $^{67}$GaCl$_3$ (5 μL, available from Fujifilm RI Pharma Co., Ltd.) was mixed with a 0.25 M acetate buffer solution (pH 5.5, 5 μL), and the mixture was allowed to stand at room temperature for 5 minutes. After mixing an NOTA-MVK-Fab solution (10 μL) therewith, the mixture was incubated at 37° C. for 1 hour. After adding a 20 mM EDTA solution (20 μL) thereto, the product was purified by the spin column method using Sephadex G-50 Fine having been equilibrated with a 0.1 M phosphate buffer solution (pH 7.0), so as to produce a metal complex compound 3-1 (which may be hereinafter referred to as "$^{67}$Ga-NOTA-MVK-Fab") shown by the following formula. A radiochemical yield of 95% or more was confirmed by TLC, CAE, and SE-HPLC.

Comparative Example 4

Production of $^{67}$Ga-NOTA-SCN-Fab $^{67}$Ga-NOTA-SCN-Fab was produced in the same manner as in Example 3 except that the NOTA-MVK-Fab solution was changed to an NOTA-SCN-Fab solution. A radiochemical yield of 95% or more was confirmed by TLC, CAE, and SE-HPLC.

Reference Example 3

Synthesis of Non-radioactive Ga-NOTA-Bn-Met

GaCl$_3$ (1.2 mg, 6.77 μmol) was dissolved in a 0.25 M sodium acetate buffer solution (50 μL), to which the compound R1 (3.0 mg, 4.51 μmol) was added. After reacting at room temperature for 1 hour, the product was purified by RP-HPLC for analysis, so as to provide non-radioactive Ga-NOTA-Bn-Met in an amount of 0.5 mg (0.83 μmol yield: 18.5%).

Non-radioactive Ga-NOTA-Bn-Met: ESI-MS m/z [M+H]$^+$ 600, Found 600.

Reference Example 4

Synthesis of $^{67}$Ga-NOTA-MVK(Bzo)

$^{67}$Ga-NOTA-MVK(Bzo) was produced in the same manner as in Example 3 except that the NOTA-MVK-Fab

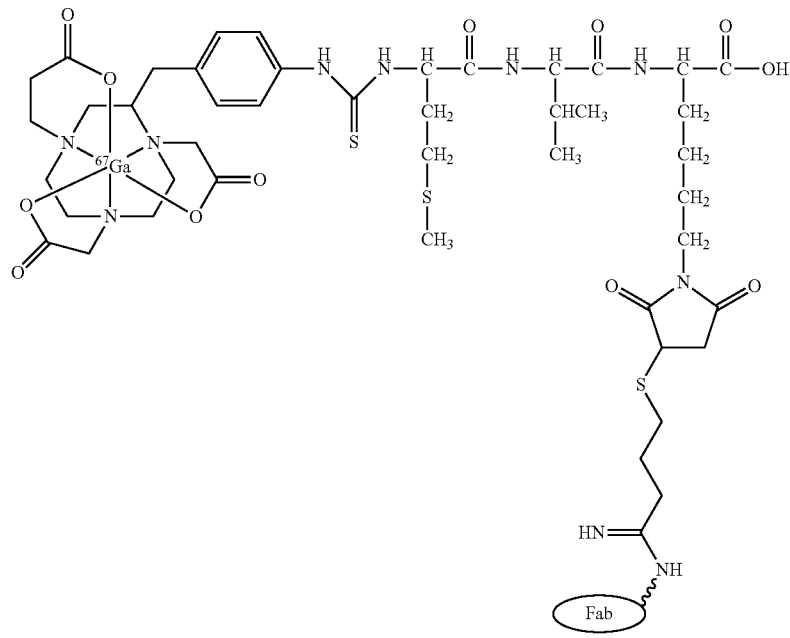

3-1: $^{67}$Ga-NOTA-MVK-Fab

Comparative Example 3

Production of $^{67}$Ga-NOTA-MI-Fab $^{67}$Ga-NOTA-MI-Fab was produced in the same manner as in Example 3 except that the NOTA-MVK-Fab solution was changed to an NOTA-MI-Fab solution. A radiochemical yield of 95% or more was confirmed by TLC, CAE, and SE-HPLC.

solution was changed to an NOTA-MVK(Bzo) solution. A radiochemical yield of 95% or more was confirmed by TLC, CAE, and SE-HPLC.

Reference Example 5

Synthesis of $^{67}$Ga-NOTA-MIK(Bzo)

$^{67}$Ga-NOTA-MIK(Bzo) was produced in the same manner as in Example 3 except that the NOTA-MVK-Fab solution was changed to an NOTA-MIK(Bzo) solution. A radiochemical yield of 95% or more was confirmed by TLC, CAE, and SE-HPLC.

Example 4

Production of $^{64}$Cu-NOTA-MVK-Fab $^{64}$CuCl$_2$ (5 μL) was mixed with a 0.1 M ammonium citrate buffer solution (pH 5.5, 5 μL), and the mixture was allowed to stand at room temperature for 5 minutes. After mixing an NOTA-MVK-Fab solution (10 μL) therewith, the mixture was incubated at 37° C. for 1 hour. After adding a 20 mM EDTA solution (20 μL) thereto, the product was purified by the spin column method using Sephadex G-50 Fine having been equilibrated with a 0.1 M phosphate buffer solution (pH 7.0), so as to produce a metal complex compound 3-2 (which may be hereinafter referred to as "$^{64}$Cu-NOTA-MVK-Fab") shown by the following formula. A radiochemical yield of 95% or more was confirmed by TLC and SE-HPLC.

diluted with the same buffer solution, so as to provide a 10% homogenate. Subsequently, after diluting with distilled water 2 times, a 1.0 M MgCl$_2$ aqueous solution was added thereto to provide a final concentration of 10 mM, and the homogenate was allowed to stand for 15 minutes. Thereafter, the homogenate was subjected to centrifugal separation at 1,900 g, and the supernatant was further subjected to centrifugal separation at 24,000 g for 30 minutes. The precipitate was again suspended in a 6 mM tris hydrochloride buffer solution (pH 7.1) containing 150 mM mannitol and 2.5 mM EGTA in an amount corresponding to 20 times the amount of the cortex, and homogenized with Teflon (trade name) homogenizer (1,000 rpm, 10 strokes). Subsequently, a 1.0 M MgCl$_2$ aqueous solution was added thereto to make a final concentration of 10 mM, the suspension liquid was allowed to stand for 15 minutes, then the homogenate was subjected to centrifugal separation at 1,900 g, and the supernatant was further subjected to centrifugal separation at 24,000 g for 30 minutes. The precipitate was again suspended in a 0.1 M phosphate buffer solution (pH

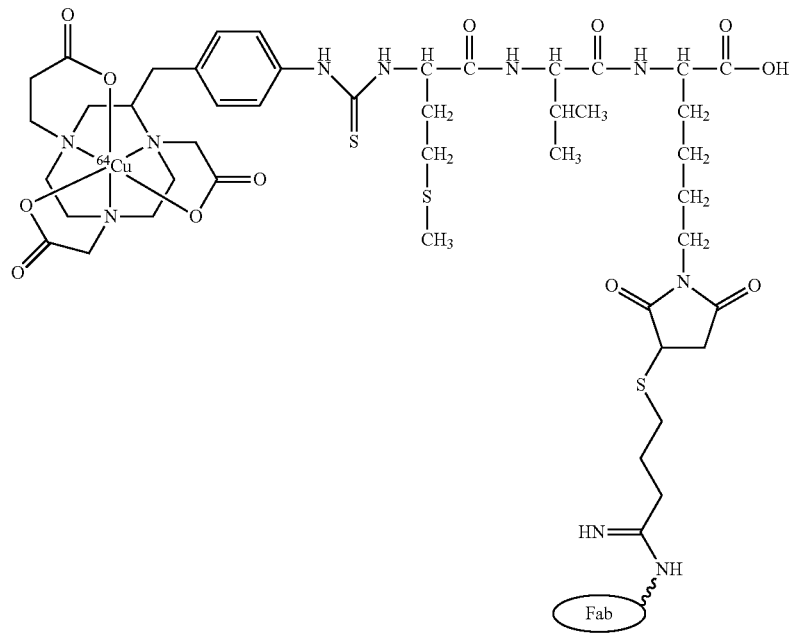

3-2: $^{64}$Cu-NOTA-MVK-Fab

Comparative Example 5

Synthesis of $^{64}$Cu-NOTA-SCN-Fab $^{67}$Ga-NOTA-SCN-Fab was produced in the same manner as in Example 4 except that the NOTA-MVK-Fab solution was changed to an NOTA-SCN-Fab solution. A radiochemical yield of 95% or more was confirmed by TLC and SE-HPLC.
[Studies on Characteristics]
[Incubation Test with BBMVs]
(Renal Brush Border Membrane Vesicles)

Renal brush border membrane vesicles were produced from a kidney of male Wistar rats (200 to 250 g). All the operations were performed on ice. From 2 to 3 times by weight of a 300 mM mannitol and a 12 mM tris hydrochloride buffer solution (pH 7.1) containing 5 mM EGTA were added to the cortex, and the mixture was homogenized with Polytron Homogenizer (PT-3100, available from Kinematica GmgH Littau, Switzerland) for 2 minutes, and 7.0) in an amount corresponding to 10 times the amount of the cortex, and homogenized with Teflon homogenizer (1,000 rpm, 10 strokes). Subsequently, the homogenate was subjected to centrifugal separation at 24,000 g for 30 minutes, so as to provide BBMVs as a precipitate. The precipitate of BBMVs was again suspended in a 0.1 M phosphate buffer solution (pH 7.0) and passed through a needle of 0.4×19 mm 10 times, so as to regulate the size of vesicles to a constant size. For the incubation test, BBMVs was used after diluting to a protein concentration of 10 mg/mL. BBMVs thus prepared was evaluated for the incorporation of the lysosome fraction by measuring the activity of β-galactosidase as a lysosome marker enzyme by using p-nitrophenyl-β-D-galacto-pyranoside. The activities of γ-glutamyl transferase and aminopeptidase were measured by using L-γ-glutamyl-p-nitroanilide and L-leucine-p-nitroanilide.
(Incubation Test)

The incubation test of BBMVs and $^{67}$Ga-NOTA-MVK (Bzo) was performed in the following manner. BBMVs (10 μL) having been prepared to have a protein concentration of 10 mg/mL was preincubated at 37° C. for 10 minutes. The excess ligands were removed from $^{67}$Ga-NOTA-MVK(Bzo) by RP-HPLC, and $^{67}$Ga-NOTA-MVK(Bzo) was again dissolved in D-PBS (−). The $^{67}$Ga-NOTA-MVK(Bzo) solution (10 μL) was added to the BBMVs solution, and incubated at 37° C. for 2 hours, and then a part of the solution was collected and analyzed by RP-TLC. 40 μL of EtOH was added thereto, the mixture was subjected to centrifugal separation at 15,000 g for 1 minute to precipitate the proteins, and then the supernatant recovered was diluted with D-PBS (−) and analyzed by RP-HPLC.

The evaluation of the metabolism by BBMVs in the presence of an enzyme inhibitor was performed in such a manner that the enzyme inhibitors (5 μL) each were added to similarly preincubated BBMVs (10 μL) to make a final concentration of 1 mM, the mixture was incubated at 37° C. for 10 minutes, and then a $^{67}$Ga-NOTA-MVK(Bzo) solution (5 μL) was added thereto. The inhibitors used were MGTA as an inhibitor for carboxypeptidase M, cilastatin as an inhibitor for renal dipeptidase, captpril as an inhibitor for angiotensin-converting enzyme, and phosphoramidon as a specific inhibitor for neutral endopeptidase. The comparison between $^{67}$Ga-NOTA-MVK(Bzo) and $^{67}$Ga-NOTA-MIK(Bzo) was performed in the same manner as above and analyzed by RP-HPLC and TLC.

As a result, $^{67}$Ga-NOTA-Met was liberated from $^{67}$Ga-NOTA-MVK(Bzo) in an amount of 80.6%, whereas $^{67}$Ga-NOTA-Met was liberated from $^{67}$Ga-NOTA-MIK(Bzo) in an amount of 94.8%. It is considered from the results that the renal accumulation is suppressed to a lower level in the case where the compound has the sequence of $^{67}$Ga-NOTA-MVK or the sequence of $^{67}$Ga-NOTA-MIK.

[Studies on Stability of Radioactive Metal-Labeled Fab in Mouse Plasma]

The radioactive metal-labeled Fab solutions (30 μL) produced in Examples and Comparative Examples each were added to mouse plasma (270 μL), and incubated at 37° C. After 1, 3, 6, and 24 hours, three solutions for each groups were analyzed by TLC and CAE, and the ratio of the radioactivity of the unchanged drug was calculated. FIG. 1 shows the results of studies on the stability of the radioactive metal-labeled Fab in mouse plasma. In the figure, the result of $^{67}$Ga-NOTA-MVK-Fab is shown by "MVK", the result of $^{67}$Ga-NOTA-MI-Fab is shown by "MI", and the result of $^{67}$Ga-NOTA-SCN-Fab is shown by "SCN" (the same is applied hereinafter). As a result, a radioactivity of 95% or more was present in the Fab fraction even after 24 hours.

[Studies on Mouse Pharmacokinetics of Radioactive Metal-Labeled Fab]

The radioactive metal-labeled Fab produced in Examples and Comparative Examples each were diluted with a phosphate buffered saline (1 mM, pH 7.4). The radioactive metal-labeled Fab solutions controlled to have an Fab concentration of 5 μg/100 μL each were administered to the mouse tail vein (0.3 μCi/100 μL/mouse). Five mice per each groups were slaughtered after 10 minutes, 30 minutes, 1 hour, 3 hours, 6 hours, and 24 hours from the administration, from which blood and organs of interest were collected and weighed, and then measured for radioactivity with the auto well gamma system. The feces and urine were collected until after 6 hours and 24 hours from the administration, and the radioactivity contained in the feces and urine were measured with the auto well gamma system.

The time-dependent changes of the biodistribution of radioactivity after administration of $^{67}$Ga-NOTA-MVK-Fab, $^{67}$Ga-NOTA-MI-Fab, and $^{67}$Ga-NOTA-SCN-Fab to normal mice are shown in Table 1. FIG. 2 shows the time-dependent changes of (a) the renal radioactivity (i.e., the time-radiation dose curve in the kidney) and (b) the radioactivity with respect to the kidney-blood ratio.

TABLE 1

| | Time after administration | | | | | |
|---|---|---|---|---|---|---|
| | 10 minutes | 30 minutes | 1 hour | 3 hours | 6 hours | 24 hours |
| | $^{67}$Ga-NOTA-MVK-Fab | | | | | |
| Blood | 26.04 ± 2.21 | 17.63 ± 1.63 | 12.63 ± 1.19 | 5.50 ± 0.41 | 2.45 ± 0.39 | 0.23 ± 0.04 |
| Liver | 3.43 ± 0.28 | 3.10 ± 0.41 | 2.51 ± 0.23 | 1.72 ± 0.16 | 1.27 ± 0.24 | 0.27 ± 0.07 |
| Spleen | 3.34 ± 0.24 | 3.27 ± 0.54 | 2.44 ± 0.24 | 1.34 ± 0.19 | 0.78 ± 0.16 | 0.22 ± 0.06 |
| Kidney | 15.38 ± 2.06 | 19.98 ± 1.86 | 17.90 ± 1.85 | 12.33 ± 1.25 | 8.43 ± 1.30 | 1.48 ± 0.18 |
| Pancreas | 0.70 ± 0.05 | 1.94 ± 2.02 | 1.06 ± 0.12 | 1.04 ± 0.13 | 0.80 ± 0.08 | 0.09 ± 0.03 |
| Heart | 4.98 ± 0.91 | 3.69 ± 2.23 | 4.04 ± 0.34 | 2.09 ± 0.16 | 1.00 ± 0.27 | 0.17 ± 0.05 |
| Lung | 11.78 ± 1.84 | 9.76 ± 1.65 | 5.90 ± 0.52 | 3.05 ± 0.52 | 1.48 ± 0.25 | 0.24 ± 0.05 |
| Stomach* | 0.34 ± 0.02 | 0.39 ± 0.07 | 0.62 ± 0.06 | 0.54 ± 0.09 | 0.44 ± 0.12 | 0.16 ± 0.16 |
| Bowel* | 2.26 ± 0.39 | 3.09 ± 0.44 | 4.33 ± 0.25 | 5.65 ± 1.05 | 10.19 ± 1.19 | 1.44 ± 1.44 |
| Muscle | 0.75 ± 0.15 | 0.94 ± 0.16 | 1.20 ± 0.08 | 0.79 ± 0.10 | 0.47 ± 0.13 | 0.04 ± 0.02 |
| Urine* | | | | | 55.65 ± 10.40 | 72.51 ± 6.01 |
| Feces* | | | | | 0.29 ± 0.36 | 16.06 ± 2.24 |
| | $^{67}$Ga-NOTA-MI-Fab | | | | | |
| Blood | 24.96 ± 1.63 | 16.59 ± 0.78 | 10.97 ± 1.22 | 3.77 ± 0.21 | 1.59 ± 0.15 | 0.15 ± 0.01 |
| Liver | 3.89 ± 0.40 | 3.22 ± 0.37 | 3.00 ± 0.41 | 2.13 ± 0.43 | 1.78 ± 0.22 | 0.74 ± 0.21 |
| Spleen | 3.18 ± 0.46 | 2.87 ± 0.55 | 2.67 ± 0.46 | 1.65 ± 0.54 | 1.02 ± 0.20 | 0.65 ± 0.26 |
| Kidney | 22.21 ± 2.40 | 36.21 ± 2.13 | 43.94 ± 3.71 | 32.44 ± 2.36 | 23.38 ± 2.11 | 10.75 ± 2.20 |
| Pancreas | 0.87 ± 0.07 | 1.02 ± 0.06 | 1.09 ± 0.22 | 0.88 ± 0.10 | 0.77 ± 0.10 | 0.21 ± 0.04 |
| Heart | 4.56 ± 0.46 | 4.89 ± 0.32 | 3.92 ± 0.43 | 1.87 ± 0.21 | 1.13 ± 0.10 | 0.42 ± 0.05 |
| Lung | 9.01 ± 1.83 | 8.11 ± 1.55 | 6.11 ± 0.90 | 2.41 ± 0.31 | 1.23 ± 0.13 | 0.30 ± 0.05 |
| Stomach* | 0.34 ± 0.04 | 0.45 ± 0.08 | 0.47 ± 0.07 | 0.42 ± 0.03 | 0.43 ± 0.16 | 0.75 ± 0.75 |
| Bowel* | 1.67 ± 0.34 | 2.84 ± 0.43 | 2.98 ± 0.52 | 4.31 ± 0.44 | 8.77 ± 2.12 | 3.12 ± 3.12 |
| Muscle | 0.75 ± 0.27 | 0.90 ± 0.07 | 0.98 ± 0.19 | 0.74 ± 0.12 | 0.55 ± 0.09 | 0.18 ± 0.04 |
| Urine* | | | | | 46.23 ± 2.33 | 68.91 ± 4.91 |
| Feces* | | | | | 0.01 ± 0.00 | 6.51 ± 2.72 |
| | $^{67}$Ga-NOTA-SCN-Fab | | | | | |
| Blood | 22.93 ± 2.37 | 13.62 ± 0.30 | 8.13 ± 0.64 | 2.91 ± 0.46 | 1.54 ± 0.29 | 0.13 ± 0.02 |
| Liver | 3.45 ± 0.22 | 2.86 ± 0.22 | 2.21 ± 0.17 | 1.79 ± 0.24 | 1.84 ± 0.22 | 0.81 ± 0.13 |
| Spleen | 2.73 ± 0.30 | 1.83 ± 0.06 | 1.25 ± 0.16 | 0.81 ± 0.12 | 0.70 ± 0.11 | 0.50 ± 0.07 |

TABLE 1-continued

| | Time after administration | | | | | |
|---|---|---|---|---|---|---|
| | 10 minutes | 30 minutes | 1 hour | 3 hours | 6 hours | 24 hours |
| Kidney | 22.51 ± 3.60 | 37.99 ± 2.92 | 46.90 ± 4.01 | 64.73 ± 9.53 | 62.91 ± 7.49 | 17.27 ± 3.45 |
| Pancreas | 0.92 ± 0.08 | 1.17 ± 0.13 | 1.12 ± 0.15 | 0.89 ± 0.15 | 0.84 ± 0.17 | 0.34 ± 0.16 |
| Heart | 4.65 ± 0.69 | 3.77 ± 0.25 | 2.80 ± 0.29 | 1.48 ± 0.24 | 0.89 ± 0.18 | 0.33 ± 0.07 |
| Lung | 9.38 ± 1.91 | 5.69 ± 0.66 | 4.02 ± 0.51 | 1.85 ± 0.28 | 1.12 ± 0.19 | 0.30 ± 0.06 |
| Stomach* | 0.51 ± 0.20 | 0.51 ± 0.06 | 0.51 ± 0.04 | 0.42 ± 0.06 | 0.31 ± 0.04 | 0.19 ± 0.19 |
| Bowel* | 2.47 ± 0.41 | 3.26 ± 0.23 | 3.18 ± 0.26 | 2.48 ± 0.44 | 2.73 ± 0.59 | 1.61 ± 1.61 |
| Muscle | 0.88 ± 0.27 | 1.10 ± 0.22 | 1.04 ± 0.36 | 0.67 ± 0.18 | 0.51 ± 0.14 | 0.12 ± 0.04 |
| Urine* | | | | | 33.98 ± 9.21 | 72.27 ± 3.65 |
| Feces* | | | | | 0.06 ± 0.06 | 3.47 ± 0.70 | unit: % ID/g,
*% ID

For $^{67}$Ga-NOTA-SCN-Fab, high radioactivity was observed in the kidney in the early stage after the administration, and high radioactivity of 63% ID/g was found even after 6 hours from the administration. For $^{67}$Ga-NOTA-MI-Fab, while the maximum value of 44% ID/g was found in the kidney after 1 hour from the administration, the radioactivity was decreased with the lapse of time, and radioactivity of 23% ID/g was observed after 6 hours. For $^{67}$Ga-NOTA-MVK-Fab, on the other hand, a lower value of renal accumulation was found in the early stage after the administration, and the radioactivity exhibited the maximum value of 20% ID/g after 30 minutes, was decreased with the lapse of time, and exhibited a significantly low value of 8% ID/g after 6 hours, as compared to $^{67}$Ga-NOTA-MI-Fab and $^{67}$Ga-NOTA-SCN-Fab. For the kidney-blood ratio, $^{67}$Ga-NOTA-MVK-Fab exhibited a significantly low value, as compared to $^{67}$Ga-NOTA-MI-Fab and $^{67}$Ga-NOTA-SCN-Fab.

[Analysis of Radioactivity in Urine]

The radioactive metal-labeled Fab produced in Examples and Comparative Examples (20 µCi, 100 µL) each were administered to the mouse tail vein, and urine accumulated until after 6 hours from the administration was filtered with a 0.45 µm filter, and then analyzed for chemical form by SE-HPLC. EtOH in an amount 2 times the recovered urine was added thereto to precipitate proteins, and after centrifugal separation at 15,000 g for 5 minutes, the supernatant was recovered. After recovering the supernatant, the pellet was rinsed with 300 µL of a 66% by mass EtOH solution (100 µL of D-PBS (−)+200 µL of EtOH), and the operation of the centrifugal separation and the recovery of the supernatant was repeated two times. The recovery ratio to the supernatant (i.e., the ratio of radioactivity recovered to the supernatant) was calculated by the expression ((activity of supernatant)/((activity of supernatant)+(activity remaining in pellet)))×100. Thereafter, the supernatant was diluted with D-PBS (−) to make an EtOH concentration of 15% by mass, and then subjected to analysis by RP-HPLC.

FIGS. 3 and 4 show the analysis results of the radioactivity excreted to urine of $^{67}$Ga-NOTA-MVK-Fab, $^{67}$Ga-NOTA-MI-Fab, and $^{67}$Ga-NOTA-SCN-Fab until after 6 hours from the administration.

FIG. 3 shows the analysis results of the radioactivity in urine by SE-HPLC until after 6 hours from the administration of (a)$^{67}$Ga-NOTA-MVK-Fab, (b) $^{67}$Ga-NOTA-MI-Fab, and (c)$^{67}$Ga-NOTA-SCN-Fab. In the SE-HPLC analysis, the radioactivity of from 70 to 80% ID/g was present in the low molecular weight fractions of a retention time of from 24 to 25 minutes in all the cases.

FIG. 4 shows the analysis results of the radioactivity in urine by RP-HPLC until after 6 hours from the administration of (a)$^{67}$Ga-NOTA-MVK-Fab, (b) $^{67}$Ga-NOTA-MI-Fab, and (c)$^{67}$Ga-NOTA-SCN-Fab, and the analysis results by RP-HPLC of (d) the authentic sample of $^{67}$Ga-NOTA-Bn-Met (non-radioactive Ga-NOTA-Bn-Met shown above) and (e) the authentic sample of $^{67}$Ga-NOTA-Bn-Lys. As a result of the analysis by RP-HPLC after removing the proteins by the ethanol precipitation method, the radioactivity of $^{67}$Ga-NOTA-SCN-Fab was eluted mainly in the fraction of a retention time of 8 minutes, which was the same as $^{67}$Ga-NOTA-Bn-Lys, but the major radioactivity of $^{67}$Ga-NOTA-MVK-Fab and $^{67}$Ga-NOTA-MI-Fab was eluted in the fraction of a retention time of 15.5 minutes, which was the same as $^{67}$Ga-NOTA-Bn-Met. The authentic sample of $^{67}$Ga-NOTA-Bn-Lys was synthesized according to the method described in Bioconjugate Chem., 1997, 8, 365-369.

It is understood from the analysis of the radioactivity in urine that the analysis by SE-HPLC shown in FIG. 3 shows that the most part of the radioactivity is excreted as the low molecular weight fraction, and the analysis by RP-HPLC shown in FIG. 4 shows that in $^{67}$Ga-NOTA-MVK-Fab, the major radioactivity in the raw molecular weight fraction is $^{67}$Ga-NOTA-Bn-Met.

[Biodistribution Test of SY Subcutaneous Tumor Model Mice]

(Cell Culture)

SY cells were cultured by using a 150 mm Cell Culture Dish-Treated (available from TrueLine). RDMI-1640 with L-glutamic acid and phenol red (available from Wako Pure Chemical Industries, Ltd.), to which FBS (available from Nippon BioSupply Center, Co., Ltd.) and penicillin/streptomycin (5,000 unit-5,000 µg/mL, Invitrogen, available from Life Technologies Japan, Ltd.) have been added to make 10% (v/v) FBS and 1% (v/v) penicillin/streptomycin, was used, and the cells were incubated at 37° C. under 5% (v/v) $CO_2$ at saturated water vapor pressure.

(Animal Experimental Model)

BALB/c-nu/nu mice (male, 8 to 10 weeks of age), in which 3×10$^6$ cells of the SY cells had been transplanted to the left femoral region, and the tumor size had grown to 0.4 to 1.0 g after 4 to 5 weeks, were used for the pharmacokinetics test using subcutaneous tumor model mice.

(Biodistribution Test)

The radioactive metal-labeled Fab produced in Examples and Comparative Examples prepared in the aforementioned manners each were diluted with a phosphate buffered saline (1 mM, pH 7.4). The radioactive metal-labeled Fab solutions having been prepared to have an Fab concentration of 5 µg/100 µL each were administered to the tail vein of the subcutaneous tumor model mice (0.3 µCi/100 µL/mouse). Five mice per each groups were slaughtered after 3 hours and 6 hours from the administration (after 6 hours only for $^{67}$Ga-NOTA-MVK-Fab and $^{67}$Ga-NOTA-SCN-Fab), from which blood and organs of interest were collected and weighed, and then measured for radioactivity with the auto well gamma system.

TABLE 2

|  | 67Ga-NOTA-MVK-Fab | | 67Ga-NOTA-MI-Fab | 67Ga-NOTA-SCN-Fab | |
| --- | --- | --- | --- | --- | --- |
|  | 3 hours | 6 hours | 3 hours | 3 hours | 6 hours |
| Blood | 4.74 ± 0.26 | 1.65 ± 0.34 | 3.84 ± 0.27 | 2.33 ± 0.12 | 0.89 ± 0.13 |
| Liver | 2.87 ± 0.36 | 2.05 ± 0.31 | 4.15 ± 0.28 | 3.16 ± 0.40 | 2.29 ± 0.42 |
| Spleen | 1.85 ± 0.12 | 1.25 ± 0.24 | 3.89 ± 0.76 | 2.66 ± 0.40 | 1.76 ± 0.12 |
| Kidney | 16.52 ± 1.64 | 15.67 ± 2.25 | 64.11 ± 8.23 | 96.63 ± 8.46 | 74.99 ± 11.81 |
| Pancreas | 0.82 ± 0.06 | 0.49 ± 0.10 | 0.70 ± 0.31 | 0.74 ± 0.10 | 0.57 ± 0.02 |
| Heart | 1.76 ± 0.14 | 0.70 ± 0.07 | 1.89 ± 0.24 | 1.61 ± 0.04 | 0.93 ± 0.05 |
| Lung | 3.59 ± 0.22 | 1.74 ± 0.36 | 2.72 ± 1.52 | 2.35 ± 0.16 | 1.28 ± 0.07 |
| Stomach* | 0.37 ± 0.12 | 0.23 ± 0.08 | 0.26 ± 0.05 | 0.24 ± 0.03 | 0.37 ± 0.10 |
| Bowel* | 6.28 ± 0.77 | 6.38 ± 0.70 | 4.21 ± 0.88 | 2.14 ± 0.12 | 3.23 ± 0.66 |
| Muscle | 0.57 ± 0.06 | 0.34 ± 0.14 | 0.48 ± 0.08 | 0.48 ± 0.05 | 0.30 ± 0.03 |
| Tumor | 10.39 ± 0.84 | 10.68 ± 2.25 | 10.35 ± 1.49 | 8.59 ± 1.84 | 7.92 ± 1.20 | unit: % ID/g,
*% ID

The biodistribution of radioactivity after administration of $^{67}$Ga-NOTA-MVK-Fab, $^{67}$Ga-NOTA-MI-Fab, and $^{67}$Ga-NOTA-SCN-Fab to the SY subcutaneous tumor model mice is shown in Table 2. FIG. 5 shows the tumor-kidney ratio of $^{67}$Ga-NOTA-MVK-Fab, $^{67}$Ga-NOTA-MI-Fab, and $^{67}$Ga-NOTA-SCN-Fab. After 3 hours from the administration, $^{67}$Ga-NOTA-MVK-Fab showed a high tumor-kidney ratio of 0.63. On the other hand, $^{67}$Ga-NOTA-MI-Fab and $^{67}$Ga-NOTA-SCN-Fab showed high radioactivity in the kidney of 64% ID/g and 97% ID/g respectively after 3 hours from the administration, and thus the tumor-kidney ratios were lower values of 0.16 and 0.09 respectively.

[SPECT Imaging]

The radioactive metal-labeled Fab produced in Examples and Comparative Examples prepared in the aforementioned manners each were diluted with a phosphate buffered saline (1 mM, pH 7.4). The radioactive metal-labeled Fab solutions having been prepared to have an Fab concentration of 5 μg/100 μL each were administered to the tail vein of the SY subcutaneous tumor model mice (100 μCi/100 μL/mouse). Two mice per each groups were imaged after 2.5 hours from the administration with an SPECT/CT instrument (SPECT4CT, available from Trifoil Imaging, CA) under condition of an opening size of 1 mm, 360-degree collection with five-pinhole collimator, 64 projections, and 1 minute per projection.

FIG. 6 shows the SPECT/CT images after the administration of $^{67}$Ga-NOTA-MVK-Fab, $^{67}$Ga-NOTA-MI-Fab, and $^{67}$Ga-NOTA-SCN-Fab to the SY subcutaneous tumor model mice. FIG. 6 shows the SPECT/CT images after 3 hours from the administration of the $^{67}$Ga-labeled Fab solutions to the SY subcutaneous tumor model mice. The tumor (T), the kidney (K), and the bladder (B) are shown. After 3 hours from the administration, $^{67}$Ga-NOTA-MVK-Fab exhibited low renal accumulation, and the tumor was clearly imaged. $^{67}$Ga-NOTA-MI-Fab and $^{67}$Ga-NOTA-SCN-Fab showed high radioactivity in the kidney although the tumor was imaged.

As described above, the radiolabeled drug exhibits low renal accumulation, and thus can enhance the sensitivity and the accuracy of radiological imaging diagnoses.

[PET Imaging]

$^{64}$Cu-NOTA-MVK-Fab and $^{64}$Cu-NOTA-Fab each were administered to normal mice (0.09 to 0.14 mCi), and after 3 hours from the administration, the mice were imaged by PET (Inveon, available from Siemens Medical Solutions, USA) over 30 minutes.

FIG. 7 shows the PET images after 3 hours from the administration of $^{64}$Cu-NOTA-MVK-Fab (which is shown as $^{64}$Cu-MVK-Fab in the figure) and $^{64}$Cu-NOTA-Fab (which is shown as $^{64}$Cu-SCN-Fab in the figure) to the normal mice. $^{64}$Cu-NOTA-MVK-Fab exhibited low renal accumulation. On the other hand, $^{64}$Ga-NOTA-SCN-Fab exhibited high radioactivity observed in the kidney.

As described above, it is understood that the radiolabeled drug relating to $^{64}$Cu-NOTA-MVK-Fab exhibits low renal accumulation.

The invention claimed is:

1. A compound or a pharmacologically allowable salt thereof, wherein the compound is represented by the following formula (1a):

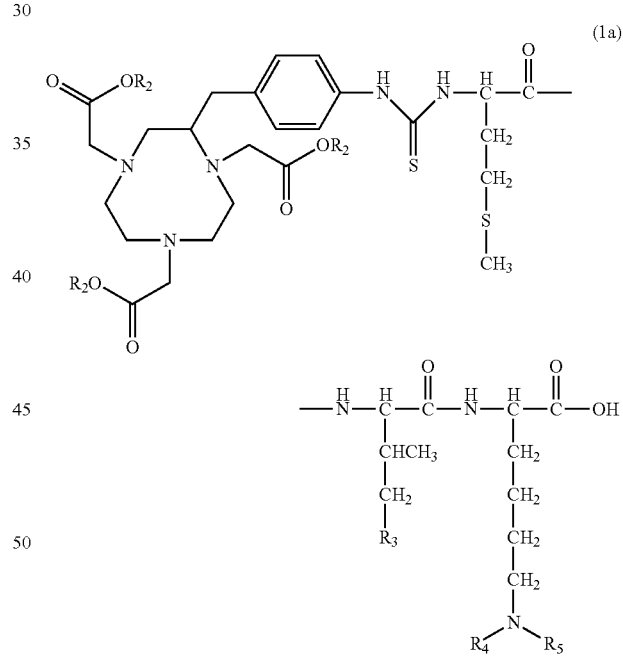

wherein $R_2$ each independently represent a hydrogen atom; $R_3$ represents a hydrogen atom; and $R_4$ and $R_5$ are either the following (i) or (ii):

(i) $R_4$ and $R_5$ each independently represent a hydrogen atom, an acyl group having from 2 to 20 carbon atoms having a functional group a, an alkyl group having from 2 to 20 carbon atoms having a functional group a, an alkylcarbamoyl group having from 2 to 20 carbon atoms having a functional group a, or an alkylthiocarbamoyl group having from 2 to 20 carbon atoms having a functional group a, wherein the functional group a is selected from the group consisting of carboxy group or an active ester thereof, a group having C=C bond, a carbamoyl group, an isothiocyanate group, and an amino group, or (ii) $R_4$ and $R_5$ form a heterocyclic ring including the adjacent nitrogen atom; and the following partial formula of the formula (1a):

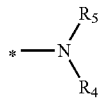

is a group represented by the following formula:

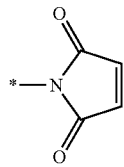

wherein * represents a bonding site.

2. A compound or a pharmacologically allowable salt thereof, comprising the compound or a pharmacologically allowable salt thereof according to claim 1 and a target molecule recognition element bonded to the compound of the pharmacologically allowable salt thereof.

3. The compound or a pharmacologically allowable salt thereof according to claim 2, wherein the target molecule recognition element is a polypeptide capable of being bound to a target molecule.

4. The compound or a pharmacologically allowable salt thereof according to claim 3, wherein the polypeptide is an Fab fragment of an antibody.

5. A metal complex compound or a pharmacologically allowable salt thereof, comprising one kind of a metal selected from a radioactive metal and a radioactive atom-labeled metal, and the compound or a pharmacologically allowable salt thereof according to claim 2, which is coordinated to the metal.

6. The metal complex compound or a pharmacologically allowable salt thereof according to claim 5, wherein the metal is $^{67}$Ga, $^{68}$Ga, $^{18}$F—Al, $^{64}$Cu, or $^{67}$Cu.

7. A drug for preparing a radiolabeled drug, comprising the compound or a pharmacologically allowable salt thereof according to claim 1, and a pharmaceutically allowable carrier.

8. A radiolabeled drug comprising the metal complex compound or a pharmacologically allowable salt thereof according to claim 5, wherein the radiolabeled drug is in the form of an aqueous solution, a frozen solution or a freeze-dried product.

* * * * *